United States Patent
Fisher et al.

(10) Patent No.: US 11,730,734 B2
(45) Date of Patent: Aug. 22, 2023

(54) USE OF ATR AND CHK1 INHIBITOR COMPOUNDS

(71) Applicant: University of Florida Research Foundation, Incorporated, Gainesville, FL (US)

(72) Inventors: Christopher Fisher, Gainesville, FL (US); Terri G. Edwards, Gainesville, FL (US); David C. Bloom, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1170 days.

(21) Appl. No.: 16/332,211

(22) PCT Filed: Sep. 12, 2017

(86) PCT No.: PCT/US2017/051176
§ 371 (c)(1),
(2) Date: Mar. 11, 2019

(87) PCT Pub. No.: WO2018/049400
PCT Pub. Date: Mar. 15, 2018

(65) Prior Publication Data
US 2019/0269682 A1 Sep. 5, 2019

Related U.S. Application Data

(60) Provisional application No. 62/393,166, filed on Sep. 12, 2016.

(51) Int. Cl.
*A61K 31/4965* (2006.01)
*A61P 31/22* (2006.01)
*A61K 31/439* (2006.01)
*A61K 31/497* (2006.01)
*A61K 31/5377* (2006.01)
*A61K 31/5517* (2006.01)
*A61K 31/505* (2006.01)
*A61K 31/4745* (2006.01)
*A61K 31/5355* (2006.01)
*A61K 31/4709* (2006.01)
*A61K 45/06* (2006.01)
*A61K 31/36* (2006.01)

(52) U.S. Cl.
CPC .......... *A61K 31/4965* (2013.01); *A61K 31/36* (2013.01); *A61K 31/439* (2013.01); *A61K 31/4709* (2013.01); *A61K 31/4745* (2013.01); *A61K 31/497* (2013.01); *A61K 31/505* (2013.01); *A61K 31/5355* (2013.01); *A61K 31/5377* (2013.01); *A61K 31/5517* (2013.01); *A61K 45/06* (2013.01); *A61P 31/22* (2018.01)

(58) Field of Classification Search
CPC .................................................. A61P 31/4965
See application file for complete search history.

(56) References Cited

U.S. PATENT DOCUMENTS

2012/0141465 A1  6/2012  Croft et al.
2013/0089626 A1  4/2013  Pollard et al.

FOREIGN PATENT DOCUMENTS

| WO | WO-2010071837 A1 * | 6/2010 | ......... A61K 31/4965 |
| WO | WO-2015057461 A2 * | 4/2015 | ............. C07K 16/40 |
| WO | WO-2018118586 A1 * | 6/2018 | |
| WO | WO-2021142230 A1 * | 7/2021 | ........... A61K 31/706 |

OTHER PUBLICATIONS

Botting et al., "H2AX phosphorylation and DNA damage kinase activity are dispensable for herpes simplex virus replication", Virology Journal, pp. 1-11, Jan. 27, 2016 (Year: 2016).*
Fokas et al., "Targeting ATR in vivo using the novel inhibitor VE-822 results in selective sensitization of pancreatic tumors to radiation", Cell Death and Disease, Dec. 6, 2012 (Year: 2012).*
International Search Report and Written Opinion, dated Jan. 12, 2018, in connection with Application No. PCT/US2017/051176.
Edwards et al. The ATM and Rad3-Related (ATR) Protein Kinase Pathway Is Activated by Herpes Simplex Virus 1 and Required for Efficient Viral Replication. J Virol. Feb. 26, 2018;92(6). pii: e01884-17. doi:10.1128/JVI.01884-17. Print Mar. 15, 2018.
Hollingworth et al. Activation of DNA Damage Response Pathways during Lytic Replication of KSHV. Viruses. Jun. 5, 2015;7(6):2908-27. doi: 10.3390/v7062752.
Sauerbrei. Infect Drug Resist. Jun. 13, 2016;9:129-41. doi: 10.2147/IDR.S96164. eCollection 2016. Review.

* cited by examiner

*Primary Examiner* — John S Kenyon
*Assistant Examiner* — Gillian A Hutter
(74) *Attorney, Agent, or Firm* — Wolf, Greenfield & Sacks, P.C.

(57) ABSTRACT

The invention relates to kinase inhibitor compounds and methods of identifying and using them. The invention further relates to pharmaceutical compositions and methods for treating or preventing herpesvirus infection and/or herpesvirus-associated diseases and disorders.

10 Claims, 13 Drawing Sheets

USE OF ATR AND CHK1 INHIBITOR COMPOUNDS

RELATED APPLICATIONS

This application is a national stage filing under 35 U.S.C. 371 of International Patent Application No. PCT/US2017/051176, filed Sep. 12, 2017, which claims the benefit of priority under 35 U.S.C. § 119(e) of U.S. provisional application number 62/393,166, filed Sep. 12, 2016, the entire contents of which re incorporated by reference herein.

STATEMENT OF RIGHTS TO INVENTIONS MADE UNDER FEDERALLY SPONSORED RESEARCH

This invention was made with government support under Grant No. AI097376, awarded by the National Institutes of Health. The government has certain rights in the invention.

BACKGROUND OF THE INVENTION

Infection by the common human pathogen herpes simplex virus (HSV) establishes life long, recurrent disease with the primary infection usually occurring within oral or genital epithelia, and latency established in the sensory ganglia innervating these tissues.

HSV-1 possesses a large, linear, double stranded genome of approximately 152 kb that encodes approximately 90 unique transcriptional units (1). Productive infection is accompanied by a highly regulated sequence of expression including immediate early (IE), early, (E), and late (L). The IE genes act as the vanguard of the productive infection to create a favorable cellular milieu for infection and to regulate subsequent E and L gene expression. The IE genes encode 5 unique proteins including ICP4, and ICP0, which play important roles in regulating subsequent viral gene expression. ICP4 is a multifunctional, DNA binding protein required for all post-IE viral gene expression. ICP0 is a non-essential multifunctional E3 ubiquitin ligase that nevertheless has important roles in regulating gene expression and negating host cell defense functions to create a favorable environment for infection. Subsequent E and L gene expression includes seven proteins essential for HSV-1 DNA replication: ICP8 (E; ssDNA binding protein), UL9 (E; origin binding protein), a 3 member helicase-primase complex (UL8 (E), UL5 (E), UL52 (E)), and the polymerase UL30 (L) and its processivity factor UL42 (E)(2).

DNA viruses have a complex relationship with the DNA damage repair (DDR) pathways, which serve to protect the host genome from point mutations, deletions, insertions, and other forms of insult. Most viruses have evolved the means to not only evade DDR surveillance but to use repair pathways to promote their own agenda (3-5). Three DDR pathways, defined by their proximal phoshoinositide-3-kinase-related kinases (PIKKs), serve as the principle mediators of the DDR. The ataxia-telangiectasia mutated (ATM) kinase senses and organizes the cellular response to double strand DNA (dsDNA) break repair, while the ATM and Rad3-related (ATR) serine/threonine protein kinase organizes the response to DNA insults such as stalled replication forks and exposure of ssDNA (6). The Chk2 and Chk1 effector kinases act downstream of ATM and ATR, respectively, to help orchestrate and integrate the DDR (7). ATM and ATR generally organize repair via homologous recombination (HR) pathways, while DNA-dependent protein kinase (DNA-PK) defines a third arm of the DDR that organizes repair via primarily via nonhomologous end joining (NHEJ)(6).

ATR, like ATM, responds to dsDNA breaks but has broader roles for repairing stalled replication forks and responding to ssDNA at sites of DNA damage (8). Unlike ATM, ATR is essential for survival of proliferating cells (9-11). ATR and ATM have redundant roles in the sensing and repair of DNA, but both are critical for dsDNA break repair and checkpoint response demonstrating they also carry non-redundant functions (10, 12). The essential ATR-interacting protein ATRIP delivers ATR to sites of ssDNA coated by RPA. These sites include stalled replication forks as well as dsDNA breaks where resection of the DNA ends occurs due to the nuclease activity of the dsDNA break-sensing Mre11-Rad50-Nbs1 (MRN) complex and its associated nucleases including CtIP, Exo1, and Dna2 (13-15).

HSV-1 has significant connections with all three of these DDR pathways (16). ICP0 is recognized to block DNA-PK function by targeting its catalytic subunit for proteosomal degradation (17-19). ATM, on the other hand is activated following HSV-1 infection (20, 21). Activation of ATM accompanies the recruitment of numerous HR elements to viral replication centers including members of the dsDNA break-sensing MRN complex (Mre11, Rad50, and Nbs1) and RAD51 (20-22), However, ICP0 targeting of the histone ubiquitin ligases RNF8 and RNF168 hinders actual DNA repair and results in increased HSV-1 fitness (23). Thus it appears that HSV-1 successfully attracts and maintains numerous HR elements in replication centers in order to promote virus replication while minimizing the antiviral properties of the pathway. Many DNA viruses, large and small, employ this strategy to promote their replication (4, 24).

Multiple reports assert that ATR is not activated following HSV-1 infection. The negative data include lack of phosphorylation of well-known ATR substrates including Chk1 (21, 25) and RPA (22, 26). It has also been reported that inhibition of the HSV-1 polymerase with PAA results in RPA phosphorylation, presumably by ATR (22, 27). Other reports have asserted that ATR is inactivated by HSV-1 based upon the observations that inhibition of the HSV-1 infection appears to block hyperphosphorylation of RPA and Chk1 induced by either hydroxyurea or UV irradiation (28). Several studies have attempted to mechanistically explain why ATR would not be activated following infection. For example, it was reported that HSV-1 infection results in sequestration of ATRIP to virus induced, chaperone-enriched (VICE) domains away from ATR, which localized to nucleoli in both infected and uninfected cells thus preventing ATR activation (26). However, this model was abandoned with the realization that the ATR and ATRIP antibodies originally employed lacked the appropriate specificity (29). Another model asserts that the HSV-1 single stranded DNA binding protein (ICP8) colocalizes to ssDNA with the helicase/primase complex (UL8/UL5/UL52) where they prevent access of the 9-1-1 complex thus blocking ATR activation (28).

In spite of these observations there remain conflicting findings to suggest that ATR might have a role to play in early stages of HSV-1 infection. For example, a recent report found that ATR-deficient fibroblasts are defective in their ability to support HSV-1 replication (30). Results described herein now establish that HSV-1 infection, specifically viral early gene transcription, activates the ATR pathway. Both ATR and Chk1 activities are found to be required for robust viral replication since multiple, chemically distinct ATR and Chk1 inhibitors significantly attenuate virus production. Together these results provide strong evidence that HSV-1 activates the ATR pathway redirecting the kinase activity of its two principal members to alternative substrates that promote virus production.

While to date certain compounds are being considered for therapeutic use in herpesvirus (e.g., HSV) treatment and prevention, these compounds suffer limitations. As such, there is a need for therapeutic agents that are useful in treating and/or preventing herpesvirus infection and symptoms thereof that are devoid of the limitations of existing agents.

SUMMARY OF THE INVENTION

The subject matter herein provides compounds and methods of using such compounds for treatment of disease and disorders, or symptoms thereof, in a subject.

In one aspect, the invention provides a method of treating a subject suffering from or susceptible to a herpesvirus infection comprising administering to subject in need thereof a therapeutically effective amount of a compound capable of inhibiting ataxia telangiectasia and Rad3-related protein (ATR)-mediated DNA-damage-checkpoint pathway. In one embodiment, the compound is capable of binding to or interacting with ATR (e.g., compounds delineated herein). In another embodiment, the compound is capable of binding to or interacting with checkpoint kinase 1 (Chk1) (e.g., compounds delineated herein).

In one aspect, the invention provides a method of inhibiting herpesvirus (e.g., HSV) replication in a subject. The method can comprise inhibition of ATR. The method can comprise inhibition of activated ATR. The method includes administering to a subject in need thereof a therapeutically effective amount of a compound delineated herein (e.g., Table 1, antibody) including salt, hydrate or solvate thereof.

In one aspect, the invention provides a method of treating a subject suffering from or susceptible to a herpesvirus (e.g., HSV) infection. The method includes administering to a subject in need thereof a therapeutically effective amount of a compound delineated herein (e.g., Table 1, antibody) including salt, hydrate or solvate thereof.

In another aspect, the invention provides a method of treating a subject suffering from or susceptible to orofacial herpes, herpes genitalis, herpes keratitis, herpesviral meningitis, herpesviral encephalitis, herpes labialis, herpetic whitlow, herpes gladiatorum, herpetic gingivostomatitis, herpes esophagitis, neonatal herpes simplex, herpetic sycosis, eczema herpeticum, herpetic keratoconjunctivitis, Herpes stromal keratitis, Bell's palsy, schizophrenia or Alzheimer's disease. The method includes administering to a subject in need thereof a therapeutically effective amount of a compound delineated herein (e.g., Table 1, antibody), including salt, hydrate or solvate thereof.

In another aspect, the invention provides a method of treating a subject suffering from or susceptible to an HSV-associated disorder or symptom thereof, comprising administering to the subject an effective amount of a compound (e.g., those delineated herein) such that the subject is treated.

In another aspect, the invention provides a packaged composition including a therapeutically effective amount of an ATR-mediated DNA-damage-checkpoint pathway inhibitor and a pharmaceutically acceptable carrier or diluent. The composition may be formulated for treating a subject suffering from or susceptible to a herpesvirus (e.g., HSV) infection and/or disorder or symptom thereof, and packaged with instructions to treat a subject suffering from or susceptible to a herpesvirus (e.g., HSV) infection and/or disorder or symptom thereof.

In one aspect, the invention provides a kit for treating or preventing a herpesvirus (e.g., HSV) infection and/or a herpesvirus- (e.g., HSV-) associated disorder or symptom in a subject is provided and includes a compound herein, pharmaceutically acceptable esters, salts, and prodrugs thereof, and instructions for use. In further aspects, the invention provides kits for inhibiting one or more components in ATR-mediated DNA-damage-checkpoint pathway, assessing the efficacy of a herpesvirus (e.g., HSV) treatment in a subject, monitoring the progress of a subject being treated with an ATR-mediated DNA-damage-checkpoint pathway inhibitor, selecting a subject with a herpesvirus (e.g., HSV) disorder for treatment with ATR-mediated DNA-damage-checkpoint pathway inhibitor, and/or treating a subject suffering from or susceptible to a herpesvirus (e.g., HSV) infection and/or a herpesvirus- (e.g., HSV-) associated disorder or symptom. In certain embodiments, the invention provides: a kit for treating or preventing a herpesvirus (e.g., HSV) infection and/or a herpesvirus- (e.g., HSV-) associated disorder or symptom in a subject, the kit comprising a compound capable of modulating (e.g., inhibiting) ATR activity or ATR binding interactions. In certain embodiments, the invention provides: a kit for treating a herpesvirus (e.g., HSV) infection and/or a herpesvirus- (e.g., HSV-) associated disorder or symptom in a subject, the kit comprising a compound capable of modulating (e.g., inhibiting) Chk1 activity or Chk1 binding interactions. In certain embodiments, the kit comprises a label or product insert comprising instructions for use of the compound or composition including the compound to treat a herpesvirus (e.g., HSV) infection or a symptom or disorder associated with a herpesvirus (e.g., HSV) infection. In some embodiments the use is administration of the compound or composition to a subject.

In one aspect, the invention provides a method of treating or preventing a herpesvirus (e.g., HSV) infection in a subject comprising administering to the subject identified as in need thereof a compound selected from Table 1 or salt, hydrate or solvate thereof. In some embodiments, the subject is administered an additional therapeutic agent. In some embodiments, the compound selected from Table 1 and the additional therapeutic agent are administered simultaneously. In some embodiments, the compound selected from Table 1 and the additional therapeutic agent are administered sequentially. In some embodiments, the HSV is HSV-1 or HSV-2.

In some embodiments, the compound selected from Table 1 or salt, hydrate or solvate thereof inhibits ATR-mediated DNA-damage-checkpoint pathway. In some embodiments, the compound selected from Table 1 or salt, hydrate or solvate thereof is an inhibitor of ATR. In some embodiments, the inhibitor of ATR is selected from the group consisting of VE-821, VE-822, AZD6738, AZ20, NVP-BEZ235, ETP-46464, NU6027, and Schisandrin B.

In some embodiments, the compound selected from Table 1 or salt, hydrate or solvate thereof is an inhibitor of Chk1. In some embodiments, the inhibitor of Chk1 is selected from the group consisting of CHIR 124, PF-00477736, AZD7762, SCH900776/MK-8776, IC83/LY2603618, LY2606368, GDC-0425, XL844, SAR-020106, and CCT-244747. In some embodiments, the compound selected from Table 1 or salt, hydrate or solvate thereof does not inhibit ATM.

In one aspect, the invention provides a method of treating a symptom or disorder associated with a herpesvirus (e.g., HSV) infection in a subject comprising administering to the subject identified as in need thereof a compound of Table 1 or salt, hydrate or solvate thereof. In some embodiments, the symptom or disorder is selected from the group consisting of orofacial herpes, herpes genitalis, herpes keratitis, herpesviral meningitis, herpesviral encephalitis, herpes labialis, herpetic whitlow, herpes gladiatorum, herpetic gingivostomatitis, herpes esophagitis, neonatal herpes simplex, herpetic sycosis, eczema herpeticum, herpetic keratoconjunctivitis, Herpes stromal keratitis, Bell's palsy, schizophrenia and Alzheimer's disease.

In one aspect, the invention provides a method for reducing herpesvirus (e.g., HSV) viral replication comprising contacting a cell with an ATR-mediated DNA-damage-checkpoint pathway inhibitor compound.

In one aspect, the invention provides a method of inhibiting a herpesvirus (e.g., HSV) in a subject identified as in need of such treatment, comprising administering a compound of Table 1 or salt, hydrate or solvate thereof.

In other aspects, the herpesvirus described herein can be HSV-1, HSV-2, Varicella zoster virus (which causes chicken-pox and shingles), Epstein-Barr virus (which causes mononucleosis), human herpesvirus 6, human herpesvirus 7, Kaposi's sarcoma-associated herpesvirus, Pseudorabies virus (cause of Aujeszky's disease in pigs), gaHV-2 (cause of Marek's disease in chickens), BHV-1 (cause of bovine infectious rhinotracheitis and pustular vulvovaginitis in cattle), and EHV-1 (cause of rhinopneumonitis in horses).

The invention also provides a pharmaceutical compositions of the compounds described herein, comprising a compound herein, or a pharmaceutically acceptable ester, salt, or prodrug thereof, together with a pharmaceutically acceptable carrier.

The invention also provides methods for designing, evaluating and identifying compounds which bind to the aforementioned binding pockets. Other embodiments of the invention are disclosed infra.

BRIEF DESCRIPTION OF THE DRAWINGS

The present invention is further described below with reference to the following non-limiting examples and with reference to the following figures, in which:

FIG. 5, panel A. Merged images of DAPI, pChk1 or pATR, and Lamin A/C labelled cells. Activated Chk1 is found within the nucleus in hydroxyurea (HU)-treated cells. Cells infected with 17+ show pChk1 and pATR distribution as defined by co-localization with Lamin A/C. Arrows point to pATR or pChk1 outside nucleus. Scale bars=10 microns. FIG. 5, panel B. Both pATR (5 h.p.i. with 17+HSV-1; MOI=10) and pChk1 (5 h.p.i. with 17+HSV-1; MOI=10) are found in the nucleus adjacent to and associated with replication centers defined by ICP4 expression, and also in the cytoplasm where they sometimes co-localize with ICP4 (arrows). Scale bars=10 microns. FIG. 5, panel C. Western blots for fractionated samples for the indicated proteins. Shown are two separately conducted fractionations conducted at 6 h.p.i. with 17+HSV-1 (MOI=10).

FIG. 6, panel A. Low magnification immunofluorescence images of ICP4 and pATR at 5 h.p.i. infection with 17+HSV-1 (MOI=10) and treatment of cells with vehicle (DMSO) or ATR inhibitor VE-822 (10 μM). Scale bars=50 microns. FIG. 6, panel B. Western blot demonstrates the ATR inhibitor VE-822 (10 μM) blocks phosphorylation of Chk1. FIG. 6, panel C. Seckel syndrome patient fibroblasts, hypomorphic for ATR, are defective for HSV-1 replication relative to control patient (IBR3) fibroblasts.

FIG. 8, panel A. Treatment with vehicle (DMSO); FIG. 8, panel B. treatment with cycloheximide, which completely suppresses pATR labeling and retards replication center formation; FIG. 8, panel C. treatment with PAA which partially blocks pATR labeling and retards replication center formation.

DETAILED DESCRIPTION OF THE INVENTION

Figure 1:
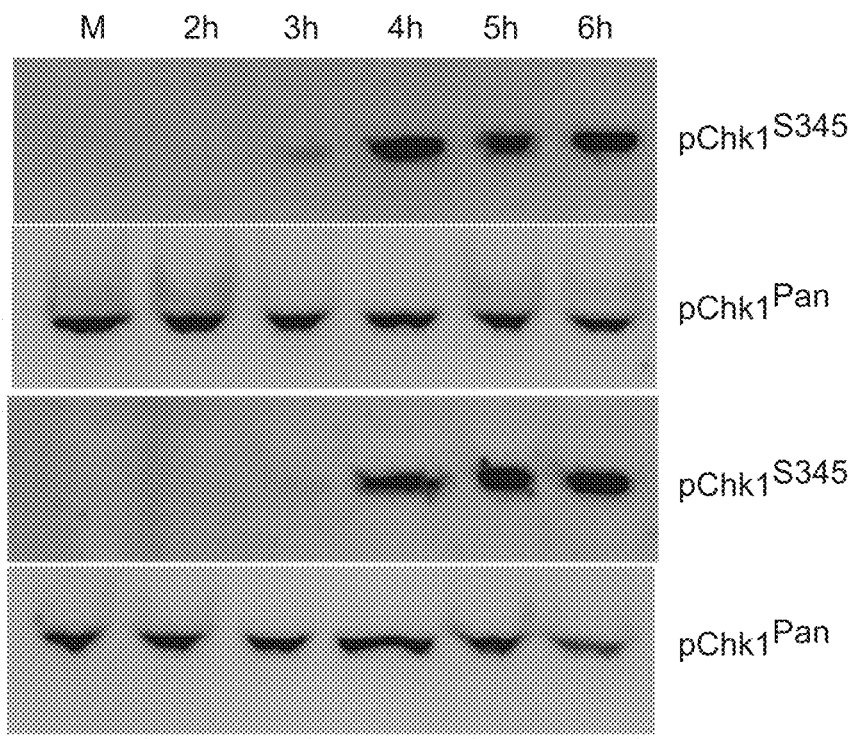
FIG. 1. Western blots demonstrating phosphorylation of pChk1S345 and pATRS428 over time following infection. Panel A. U2OS (top) or Vero (bottom) cells were infected with 17+HSV-1 (MOI=10) and prepared for Western blotting at the indicated h.p.i. with the indicated antibodies recognizing pChk1(S345) or Chk1(Pan). Chk1 activation is first detected at 3 h.p.i. in both cell types. Panel B. U2OS cells were infected with 17+HSV-1 (MOI=10) and prepared for Western blotting at the indicated h.p.i. with the indicated antibodies recognizing ATM(S1981), ATM(Pan), ATR (S428), and ATR(Pan). ATM activation is first detected at the end of the pre-incubation period (0 h.p.i.) while evidence of ATR phosphorylation is first seen at 3 h.p.i.
Figure 1:
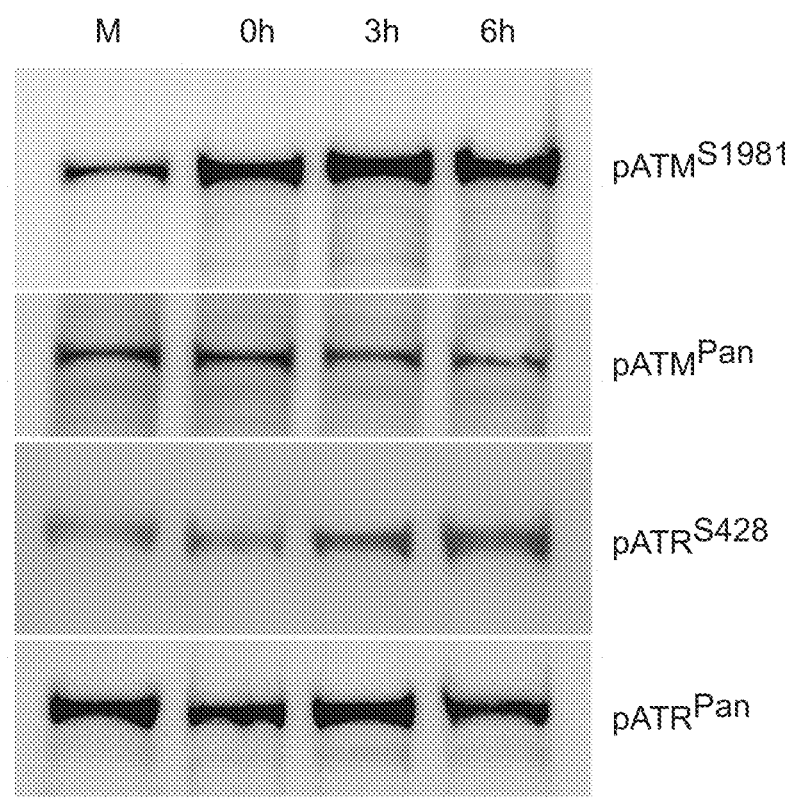

The present inventors have now discovered a therapeutic strategy that addresses inhibition of ATR-mediated DNA-damage-checkpoint pathway by targeting ATR pathway interactions. Such interactions are relevant for modulation of HSV disease.

The present invention also relates, at least in part, to the discovery that the compounds delineated herein demonstrate selective interactions with certain targets (e.g., selective for ATR or Chk1) for HSV infection and/or associated disorder therapy.

1. Definitions

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred, although topical application may address potential toxicity issues. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, acylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a disorder delineated herein. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "cell proliferative disorder" includes disorders involving the undesired or uncontrolled proliferation of a cell. Examples of such disorders include, but are not limited to, tumors or cancers (e.g., lung (small cell and non-small cell), thyroid, prostate, pancreatic, breast or colon), sarcoma, leukemia, myeloma, lymphoma, or melanoma.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-(C1-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result.

The term "obtaining" as in "obtaining a compound" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a disorder delineated herein The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a herpesvirus (e.g., HSV) disorder or who could otherwise benefit from the administration of a compound of the invention of the invention, such as human and non-human animals. Preferred humans include human patients suffering from or prone to suffering from a herpesvirus (e.g., HSV) disorder, disorder delineated herein, or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to a HSV disorder" is meant to include subjects at risk of developing disorder of HSV, e.g., HSV, i.e., subjects suffering from HSV, subjects having a family or medical history of HSV disorder, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention of the invention refers to an amount of an agent which is effective, upon single or multiple dose in ameliorating a herpesvirus (e.g., HSV) disorder, or in prolonging the survivability of the patient with such a herpesvirus (e.g., HSV) disorder beyond that expected in the absence of such treatment.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides compounds capable of modulating (e.g., inhibiting or stimulating) (directly or indirectly) ATR-binding activity and methods using the compounds thereof.

In one embodiment, the invention provides a compound capable of modulating ATR-mediated protein binding; and pharmaceutically acceptable esters, salts, and prodrugs thereof. In some embodiments, compounds include antibodies as described herein.

Certain preferred compounds include compounds specifically delineated herein:

TABLE 1

| ATR Pathway Inhibitor Compounds: | |
|---|---|
| Compound Name/Function | Structure |
| VE-821 (ATR Inhibitor) | |
| VE-822 (ATR Inhibitor) | |
| AZD6738 (ATR Inhibitor) | |
| AZ20 (ATR Inhibitor) | |

TABLE 1-continued

ATR Pathway Inhibitor Compounds:

| Compound Name/Function | Structure |
|---|---|
| NVP-BEZ235 (ATR Inhibitor) | 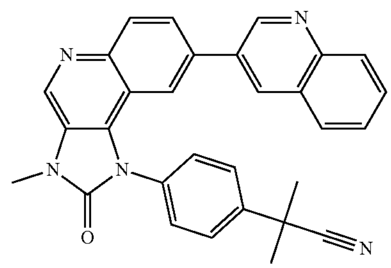 [SMILES: Cn1c(=O)n(-c2ccc(C(C)(C)C#N)cc2)c2c3cc(-c4cnc5ccccc5c4)ccc3ncc21] |
| ETP-46464 (ATR Inhibitor) | 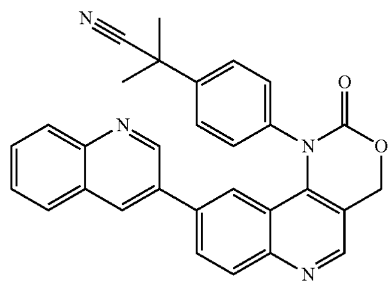 [SMILES: CC(C)(C#N)c1ccc(N2C(=O)OCc3cnc4ccc(-c5cnc6ccccc6c5)cc4c32)cc1] |
| NU6027 (ATR Inhibitor) | 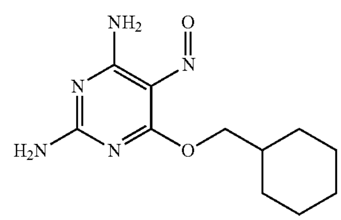 [SMILES: Nc1nc(N)c(N=O)c(OCC2CCCCC2)n1] |
| Schisandrin B (ATR Inhibitor) | 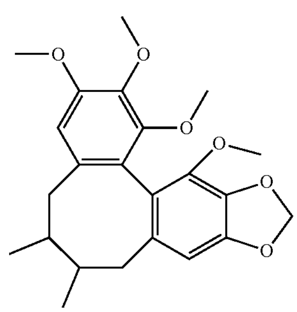 [SMILES: COc1cc2c(c(OC)c1OC)-c1c(cc3c(c1OC)OCO3)CC(C)C(C)C2] |
| CHIR 124 (Chk1 Inhibitor) | 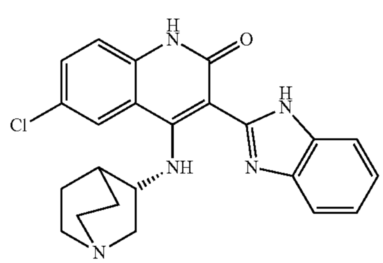 |

TABLE 1-continued

ATR Pathway Inhibitor Compounds:

| Compound Name/Function | Structure |
|---|---|
| PF-00477736 (Chk1 Inhibitor) | 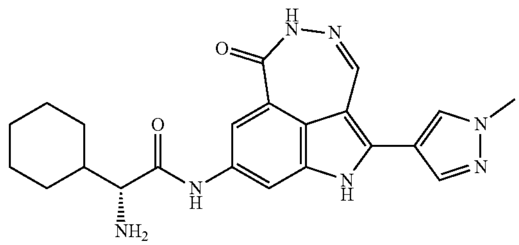 [SMILES: Cn1cc(-c2[nH]c3cc(NC(=O)[C@H](N)C4CCCCC4)cc4c3c2C=NNC4=O)cn1] |
| AZD7762 (Chk1 Inhibitor) | 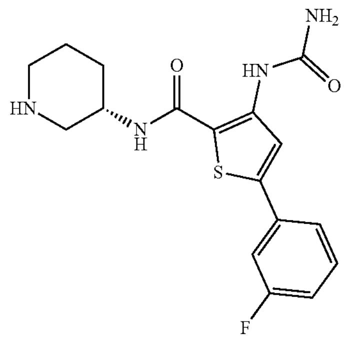 [SMILES: NC(=O)Nc1cc(-c2cccc(F)c2)sc1C(=O)N[C@H]1CCCNC1] |
| SCH900776/MK-8776 (Chk1 Inhibitor) | 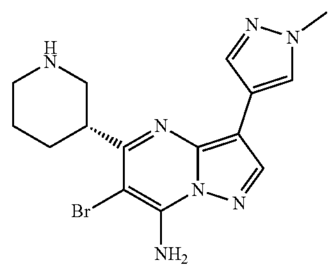 [SMILES: Cn1cc(-c2cnn3c(N)c(Br)c([C@@H]4CCCNC4)nc23)cn1] |
| IC83/LY2603618 (Chk1 Inhibitor) | 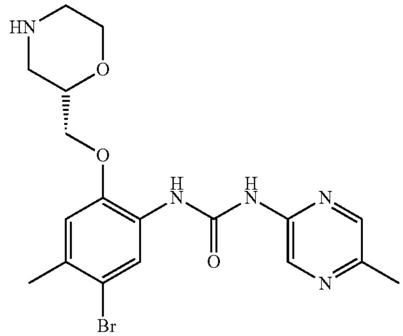 |
| LY2606368 (Chk1 Inhibitor) | 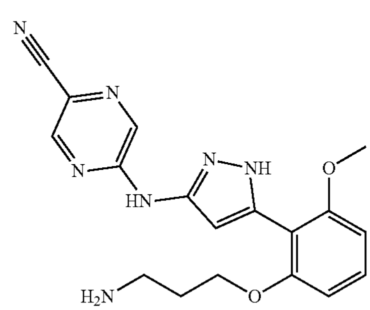 [SMILES: COc1cccc(OCCCN)c1-c1cc(Nc2cnc(C#N)cn2)n[nH]1] |

TABLE 1-continued

ATR Pathway Inhibitor Compounds:

| Compound Name/Function | Structure |
|---|---|
| GDC-0425 (Chk1 Inhibitor) | 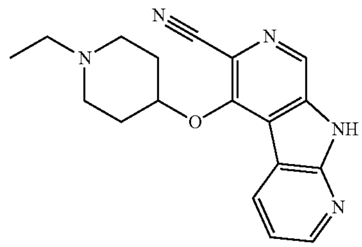 [SMILES: CCN1CCC(Oc2c(C#N)ncc3[nH]c4ncccc4c23)CC1] |
| XL844 (Chk1 Inhibitor) | 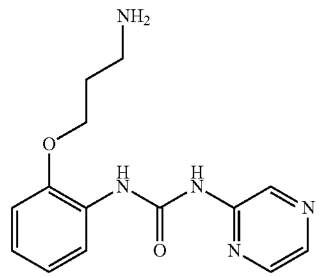 [SMILES: NCCCOc1ccccc1NC(=O)Nc1cnccn1] |
| SAR-020106 (Chk1 Inhibitor) | 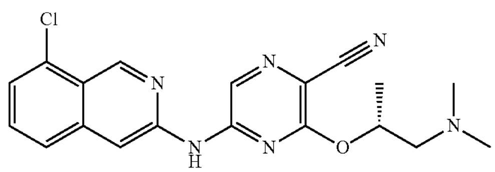 [SMILES: C[C@H](CN(C)C)Oc1nc(Nc2cc3cccc(Cl)c3cn2)cnc1C#N] |
| CCT-244747 (Chk1 Inhibitor) | 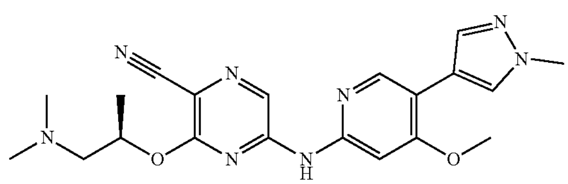 |

The invention also relates to the pharmaceutically acceptable salts and esters of the above-mentioned compounds.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

3. Uses of the Compounds of the Invention

In certain aspects, the disclosure provides compositions and methods useful for treating or preventing herpesvirus infection and/or an herpesvirus-associated disease or disorder. Among other aspects, the disclosure provides compositions and methods useful for treating or preventing a herpesvirus (e.g., HSV) infection and/or a herpesvirus- (e.g., HSV-) associated disease or disorder. In some embodiments, the HSV is HSV-1. In some embodiments, the HSV is HSV-2.

In one embodiment, the invention provides methods for treating a subject for herpesvirus (e.g., HSV) infection and/or herpesvirus- (e.g., HSV-) associated disorder by administering to the subject an effective amount of a compound capable of disrupting a component of the ATR-mediated DNA-damage-checkpoint pathway. In some embodiments, the compound does not inhibit ataxia telangiectasia mutated (ATM).

In this embodiment, the compounds of the invention may either directly or indirectly modulate ATR or ATR activity, Chk1 or Chk1 activity, and a subject can be contacted with a compound of the invention to inhibit disease or disorder processes or modulation of the herpesvirus (e.g., HSV) metabolic cascade. Contacting cells or administering the compounds of the invention to a subject is one method of treating a cell or a subject suffering from or susceptible to herpesvirus (e.g., HSV) infection or an herpesvirus- (e.g., HSV-) associated disorder.

In some embodiments, methods and compositions provided herein are useful for treating one or more diseases or disorders associated with herpesvirus (e.g., HSV). For example, in some embodiments, the one or more diseases or disorders can include orofacial herpes, herpes genitalis, herpes keratitis, herpesviral meningitis, herpesviral encephalitis, herpes labialis, herpetic whitlow, herpes gladiatorum, herpetic gingivostomatitis, herpes esophagitis, neonatal herpes simplex, herpetic sycosis, eczema herpeticum, herpetic keratoconjunctivitis, Herpes stromal keratitis, Bell's palsy, schizophrenia and Alzheimer's disease.

In certain embodiments, the methods of the invention include administering to a subject a therapeutically effective amount of a compound of the invention in combination with another pharmaceutically active compound. Examples of pharmaceutically active compounds include compounds known to treat viruses and viral disorders, e.g., acyclovir, valaciclovir (valacyclovir), famciclovir, ganciclovir, foscarnet, trifluridine, penciclovir, docosanol, zoster-immune globulin (ZIG), vidarabine, VZV immune globulin, etc. Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of disease or disorders in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

The identification of those patients who are in need of prophylactic treatment for herpesvirus (e.g., HSV) infection and/or disorders is well within the ability and knowledge of one skilled in the art. Certain of the methods for identification of patients which are at risk of herpesvirus (e.g., HSV) infection and/or disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of an herpesvirus (e.g., HSV) infection and/or herpesvirus- (e.g., HSV-) associated disorder by methods well known in the art (e.g., determining markers where the herpesvirus (e.g., HSV) infection and/or herpesvirus- (e.g., HSV-) associated disorder is present) and then administering a therapeutically effective amount of an inhibitor of cell proliferation (e.g., those described herein) according to the invention to the subject. After an appropriate period of time after the administration of the compound (e.g., 1 day, 1 week, 2 weeks, one month, six months), the extent of the herpesvirus (e.g., HSV) infection and/or herpesvirus- (e.g., HSV-) associated disorder is determined again. The modulation (e.g., decrease) of the extent or invasiveness of the herpesvirus (e.g., HSV) disorder indicates efficacy of the treatment. The extent or invasiveness of the herpesvirus (e.g., HSV) infection and/or herpesvirus- (e.g., HSV-) associated disorder may be determined periodically throughout treatment. For example, the extent or invasiveness of the herpesvirus (e.g., HSV) infection and/or herpesvirus- (e.g., HSV-) associated disorder may be checked every few hours, days or weeks to assess the further efficacy of the treatment. A decrease in extent or invasiveness of the herpesvirus (e.g., HSV) infection and/or herpesvirus- (e.g., HSV-) associated disorder indicates that the treatment is efficacious. The method described may be used to screen or select patients that may benefit from treatment with an inhibitor of ATR-mediated DNA-damage-checkpoint pathway.

As used herein, "obtaining a biological sample from a subject," includes obtaining a sample for use in the methods described herein. A biological sample is described above.

In another aspect, a compound of the invention is packaged in a therapeutically effective amount with a pharmaceutically acceptable carrier or diluent. The composition may be formulated for treating a subject suffering from or susceptible to a herpesvirus (e.g., HSV) infection and/or herpesvirus- (e.g., HSV-) associated disorder, and packaged with instructions to treat a subject suffering from or susceptible to herpesvirus (e.g., HSV) infection and/or herpesvirus- (e.g., HSV-) associated disorder.

In another aspect, methods of inhibiting a herpesvirus (e.g., HSV) infection and/or herpesvirus- (e.g., HSV-) associated disorder in a subject include administering an effective amount of a compound of the invention (i.e., a compound described herein) to the subject. In some embodiments, the compound includes a antibody as described herein. The administration may be by any route of administering known in the pharmaceutical arts. The subject may have a herpesvirus (e.g., HSV) infection and/or herpesvirus- (e.g., HSV-) associated disorder, may be at risk of developing a herpesvirus (e.g., HSV) infection and/or herpesvirus- (e.g., HSV-) associated disorder, or may need prophylactic treatment prior to anticipated or unanticipated exposure to a conditions capable of increasing susceptibility to an herpesvirus (e.g., HSV) infection and/or herpesvirus- (e.g., HSV-) associated disorder, e.g., exposure to carcinogens or to ionizing radiation.

The subject may be at risk of herpesvirus (e.g., HSV) infection and/or herpesvirus- (e.g., HSV-) associated disorder, may be exhibiting symptoms of an herpesvirus- (e.g., HSV-) associated disorder, may be susceptible to a herpesvirus (e.g., HSV) infection and/or herpesvirus- (e.g., HSV-) associated disorder and/or may have been diagnosed with a herpesvirus (e.g., HSV) infection and/or herpesvirus- (e.g., HSV-) associated disorder.

If the modulation of the status indicates that the subject may have a favorable clinical response to the treatment, the subject may be treated with the compound. For example, the subject can be administered therapeutically effective dose or doses of the compound.

Kits of the invention include kits for treating a herpesvirus (e.g., HSV) infection and/or herpesvirus- (e.g., HSV-) associated disorder in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of an treatment for a herpesvirus (e.g., HSV) infection and/or herpesvirus- (e.g., HSV-) associated disorder may be packaged with a kit for monitoring the progress of a subject being treated for a herpesvirus (e.g., HSV) infection and/or herpesvirus- (e.g., HSV-) associated disorder according to the invention.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like.

The present method can be performed on cells in culture, e.g. in vitro or ex vivo, or on cells present in an animal subject, e.g., in vivo. Compound of the invention can be initially tested in vitro using cells or other mammalian or non-mammalian animal models. Alternatively, the effects of compound of the invention can be characterized in vivo using animals models.

4. Pharmaceutical Compositions

The invention also provides a pharmaceutical composition, comprising an effective amount of a compound and a pharmaceutically acceptable carrier. In a further embodiment, the effective amount is effective to treat a herpesvirus (e.g., HSV) infection and/or herpesvirus- (e.g., HSV-) associated disorder, as described previously. The pharmaceutical composition can be for human or veterinary use.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; ($1_3$) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

EXAMPLES

The invention is further illustrated by the following examples which are intended to illustrate but not limit the scope of the invention.

The ATM and Rad3-related (ATR) protein kinase, and its downstream effector Chk1, are key sensors and organizers of the DNA damage response (DDR) to a variety of insults. Previous studies of Herpes Simplex Virus 1 (HSV-1) have failed to show evidence for activation of the ATR pathway. Using antibodies recognizing pChk1(S345), a site phosphorylated by ATR, we observed intense immunolabelling using multiple HSV-1 strains and cell types. Western blots confirmed that both ATR and Chk1 were activated by 3 h.p.i., and that ATR-specific inhibitors blocked activation and maturation of viral replication centers. Both pATR and pChk1 were localized to the nucleus within viral replication domains, or associated with their periphery, by 3 h.p.i. Significant levels of pATR and pChk1 were also detected throughout the cytoplasm where they co-localized with ICP4. Proximity ligation assays show that pATR and pChk1 are closely associated with ICP4 and ICP0 in the cytoplasm, presumably in a multi-protein complex, by 3 h.p.i. Multiple, chemically distinct ATR and Chk1 inhibitors inhibit HSV-1 replication and virion production, while inhibitors of ATM, Chk2, and DNA-PK are ineffective. Together our data strongly suggest that HSV-1 activates the ATR pathway at early stages of infection, and that ATR and Chk1 kinase activities play important roles in HSV-1 replication fitness.

Viruses have evolved complex associations with cellular DNA damage response (DDR) pathways, which sense troublesome DNA structures formed during infection. The first evidence for activation of a key DDR pathway by HSV-1 is presented. Both pATR and its downstream target pChk1 are activated robustly by 3 h.p.i. Both proteins are found in the nucleus associated with viral replication compartments, and in the cytoplasm associated with viral proteins. We demonstrate that both ATR and Chk1 kinase activities are important for viral replication. The findings suggest that HSV-1 activates ATR and Chk1 during early stages of infection, and utilizes the kinases to promote its own replication. The observation may be exploitable for antiviral approaches.

Example 1: The ATR and Chk1 Activities

Materials and Methods
Viruses and Cell Lines:
Several HSV-1 viral strains were used in this study: 17syn+ KOS/M, McIntyre and McKrae, KD6. U2OS cells were maintained in McCoy's 5 A media (Corning, catalog no. 10-050-CV) supplemented with 10% FBS and 1× Penicillin Streptomycin Glutamine (PSG; Gibco catalog no. 10378). Vero, and human fetal lung (HFL) cells were maintained in DMEM (Corning, catalog no. 10-013-CV) with 10% FBS and 1×PSG). Rabbit skin cells (60) were maintained in MEM (Gibco, catalog no. 11700077) plus 5% bovine serum and 1×PSG. Seckel patient (ATR-) (61) and normal patient (1BR3) fibroblast cell lines immortalized with hTert (kindly provided by Peggy Jeggo, University of Sussex) were maintained in Eagle's MEM supplemented with 10% FBS and 1×PSG using a 1:2 split ratio. Cells were plated in 24-well dishes at a density of $1.5 \times 10^5$ cells per well and the following day infected with 17syn+ at an MOI=0.01. Following incubation at the indicated time-points, cells were harvested and DNA isolated using DNAzol following the manufacturer's recommendation. 20 ng of total DNA was analyzed for HSV-1 genomes by Q-PCR (see below). The LUHMES neuronal cell line was purchased from ATCC (catalog no. CRL-2927) and cultured on poly-1-ornithine hydrobromide (Sigma, catalog no. P3655)+fibronectin (Sigma, catalog no. F2006) coated flasks, plates and coverslips in proliferation media (DMEM-F12, ATCC, catalog no. 30-2006; 1×N-2 Supplement, ThermoFisher Sci., catalog no. 17502048; 40 ng/mL recombinant human FGF-basic, Peprotech, catalog no. 100-18B-100UG) as described in Scholz et al. Experiments were conducted on LUHMES following at least five days of differentiation in proliferation media supplemented with tetracycline hydrochloride at 1 ug/mL (Sigma catalog no. T7660), N6,2'-O-Dibutyryladenosine 3',5'-cyclic monophosphate sodium salt at 1 mM final (Sigma, catalog no. D0627) and recombinant human GDNF at 2 ng/mL (R&D Systems, catalog no. 212-GD-010).

Inhibitors:
The following ATR inhibitors were purchased from Selleckchem and used at 10 μM final: VE-822 (catalog no. 57102 Batch No. 1), VE-821 (catalog no. S8007), AZD6738 (catalog no. S7693), and AZ20 (catalog no. S7050). Chk1 inhibitors were purchased from Axon Medchem and used at 250 nM final concentration (CHIR 124, catalog no. Axon 1636 and PF 477736, catalog no. Axon 1379). Other chemical inhibitors and their final concentrations described in this study are: Chk2 inhibitor II hydrate (5 μM, Sigma, catalog no. C3742), ATM inhibitor KU55933 (10 μM, Tocris, catalog no. 3544), DNA-PK inhibitor NU7441 (1 μM, Tocris, catalog no. 3712), and aphidicolin (4 μM, Sigma, catalog no. A0781).

Antibodies:
The following antibodies were used in this study: Phospho-Chk1 (Ser345) (133D3) Rabbit mAb (Cell Signaling, catalog no. 2348); Phospho-Chk1 (Ser345) Rabbit polyclonal (ThermoFisher Sci., catalog no. PAS-34625); Chk1 (2G1D5) mouse mAb (Cell Signaling, catalog no. 2360); α-HSV-1 ICP4 hybridoma; Tubulin (α+β) mouse mAb (abcam, catalog no. ab44928); α-HSV-1 ICP8 mouse mAb 11E2 (abcam, catalog no. ab20194), α-HSV-1 ICP0 mouse mAb 5H7 (abcam, catalog no. ab6513); Phospho-ATR (Ser428) Rabbit polyclonal Ab (Cell Signaling, catalog no. 2853); Phospho-ATR (Ser428) Rabbit polyclonal Ab (ThermoFisher Sci., catalog no. 720107); ATR (H-300) rabbit polyclonal Ab (Santa Cruz, catalog no. sc-28901); Phospho-ATM (Ser1981) Rabbit mAb EP1890Y (abcam, catalog no. ab81292); ATM mouse mAb2C1(1A1) (abcam, catalog no. ab78); Lamin A/C (4C11) mouse mAb (Cell Signaling, catalog no. 4777).

Antiviral Assays, HSV-1 Titering and Q-PCR:
Cells were plated at 5×105 cells per well in 6-well plates and the following morning incubated with inhibitors. Following 1 h pre-incubation with inhibitors, cells were infected with HSV-1 at an MOI=0.1 in a volume of 200 uL for 1 h, viral inoculum removed, and cells overlaid with media containing fresh inhibitors, and cultured for 48 h. Following 48 h, cells and supernatant were harvested by scraping, separated into two Eppendorf tubes, and centrifuged at 10,000×g for 40 min. The cell pellet from one tube was used for extraction of DNA (DNazol according to manufacturer's recommendation, ThermoFisher Sci. catalog no. 10503027) and the second pellet was re-suspended in 200 uL serum-free MEM, freeze-thawed 3×, and virus titered on rabbit skin cells. For HSV-1 titering, rabbit skin cells were plated at 150,000 cells/well of 24-well plates and the following day infected with 10-fold serial dilutions of virus harvested from antiviral experiments. Cells were incubated for 48 h, stained with 1% crystal violet solution, and plaques counted from three separate wells for each experimental sample. Q-PCR was conducted using 20 ng input DNA, TaqMan® Fast Universal PCR 2× Master Mix (Applied Biosystems, catalog no. 4352041) along with TaqMan probes and target-specific primers (Applied Biosystems, Assays by Design part no. 4331348) against HSV-1 polymerase. Samples were run on a StepOnePlus Real-Time PCR System (Applied Biosystems) using fast cycling: denaturation at 95° C. for 20 sec followed by 40 cycles at 95° C. for 1 sec and 60° C. for 20 sec. Additional experimental compounds were also tested as follows: (57) Cyclohexamide (Sigma, catalog no. C7698) or DMSO vehicle was added to the overlay media at 50 ug/mL and the infection allowed to proceed for 5 h. (2) For replication inhibition, phosphonoacetic acid (PAA) was added at time of virus adsorption and included in overlay media at 400 ug/mL for 5 h. (3) A final [3 mM] hydroxyurea was added at the time of cell plating and incubated for 18 h.

Western Blotting:
$5 \times 10^5$ cells were plated on 6-well plates and infected the following day with 17syn+(MOI=10). At the indicated times, cells were lysed in buffer containing 1% NP-40, 150 mM sodium chloride, 20 mM Tris-HCL pH 8.0, 2 mM EDTA, and 5% glycerol supplemented with phosphatase and protease inhibitor cocktails (Roche, PhosSTOP tablets; catalog no. 04906837001; ThermoFisherSci., Halt Protease Inhibitor Cocktail, catalog no. 1862209). For SDS-PAGE, 20 ug of protein was mixed with NuPAGE 4×LDS sample buffer (ThermoFisher Sci., catalog no. NP0007) along with NuPAGE Sample Reducing Agent (ThermoFisher Sci., catalog no. NP0004) and run on 4-12% Bis-Tris NuPAGE gels (ThermoFisher Sci.) with NuPAGE MOPS SDS running buffer (ThermoFisher Sci., catalog no. NP000102). Gels were transferred onto 0.22 µm PVDF in Towbin buffer (0.2 M Glycine, 25 mM Tris Base) containing 20% MeOH for 2 h under constant voltage (30V), the membrane blocked with 5% non-fat dry milk (NFDM)-TBST (20 mM Tris-HCL pH 7.4, 150 mM NaCl, 0.1% Tween-20) and probed with antibodies diluted in 1% NFDM-TBST overnight at 4° C. For ATR and ATM western blots, samples were processed as above except DTT (50 mM, Cell Signaling, catalog no. 7016) was used as the reducing agent and samples were run on NuPAGE Novex 3-8% Tris-acetate gels (ThermoFisher Sci.) with NuPAGE Tris-acetate SDS running buffer (ThermoFisher Sci., catalog no. LA0041). Gels were transferred under constant current (7.5 mA/cm2) for 24 h at 4° C. with Towbin buffer (0.2M Glycine, 25 mM Tris base) containing 0.1% SDS for ATR blotting or 0.05% SDS plus 20% MeOH for ATM blotting onto PVDF (0.45 µm), the membranes were then allowed to dry at RT, reactivated with MeOH, blocked in 5% NFDM-TBST containing phosphatase inhibitors (Roche, PhoSTOP tablets) and incubated overnight at 4° C. the specified antibody. Secondary antibody detection was performed by incubating blots with Pierce Goat anti-rabbit Poly-HRP (ThermoFisher Sci., catalog no. 32260) or Pierce Goat anti-mouse Poly-HRP (ThermoFisher Sci., catalog no. 32230) at 1:5000 diluted in 5% NFDM-TBST. Blots were developed with chemiluminescent substrate (Pierce ECL Western Blotting Substrate, catalog no. 32209) and imaged with a GE ImageQuant LAS4000 instrument. For re-probing, membranes were stripped with 6M guanidine hydrochloride, 0.2% NP-40, 0.1M βME, 20 mM Tris-HCL pH 7.4 (2×5' RT followed by 4×3' washes with TBST).

For partitioning of RIPA soluble and insoluble fractions, cells were plated and infected as described above and cells were lysed 30 min on ice with RIPA buffer (150 mM NaCl, 1% NP40, 0.1% SDS, 50 mM Tris-HCL pH 7.4). Cells were scraped into 1.5 mL Eppendorf tubes and centrifuged at 13,500 rpm for 15 min at 4° C. and the supernatant collected. The RIPA insoluble pellet was washed 3× with RIPA buffer and re-suspended in NuPAGE 4×LDS sample buffer diluted to 1× with water. β-mercaptoethanol (βME) was added to both the RIPA-soluble and insoluble fractions at a final concentration of 12.5% and samples run on 4-12% Bis-tris gels with MOPS SDS running buffer as described above. For re-probing, membranes were stripped with 6M guanidine hydrochloride, 0.2% NP-40, 0.1 M βME, 20 mM Tris-HCL pH 7.4 (2×5' RT followed by 4×3' washes with TBST).

Immunofluorescence and Microscopy:

U2OS cells were plated onto coverslips at 75,000 cells per well of 24-well plates and the following day infected at an MOI=10 for the indicated times.

Initial immunofluorescence experiments with paraformaldehyde-fixed cells found that rabbit phospho-specific antibodies bound non-specifically to a juxtanuclear domain associated with the microtubule-organizing center (MTOC) (see Results). Thereafter, cells were processed for immunofluorescence in one of two ways that incorporated an Fc receptor blocking step: (1) cells were fractionated in situ by pre-extraction following previously published procedures; briefly, cells were incubated in Cytoskeleton Buffer (CB; 100 mM PIPES, 300 mM sucrose, 100 mM NaCl, 3 mM $MgCl_2$, 1 mM EGTA) for 5 min on ice followed by incubation in Cytoskeleton Stripping Buffer (CSK; 10 mM Tri-HCL pH 7.4, 10 mM NaCl, 3 mM $MgCl_2$, 1% Tween-40, 1% Tween-20, 0.5% sodium deoxycholate) for 5 min on ice. Cells were then washed 3× with PBS and fixed with Streck fixative (150 mM 2-bromo-2-nitro-1,3-propanediol, 108 mM diazolidinyl urea, 10 mM sodium citrate, 50 mM EDTA) for 30 min at RT, washed with PBS, and permeabilized with 0.5% Triton X-100 in 100 mM Tris-HCL pH 7.4 plus 50 mM EDTA for 15 min at RT. Cells were then incubated sequentially with Fc Receptor Blocker (Innovex Biosciences, catalog no. NB309) for 30 min at RT followed by blocking buffer (5% goat serum, 0.1% NP-40, 20 mM Tris-HCL pH 7.4, 150 mM NaCl) for 30 min at RT. (2) In some cases cells were fixed in 3.7% paraformaldehyde in PBS for 5 min at RT followed by blocking with Fc Receptor Blocker and blocking buffer as above.

Cells were processed for IF as described above. All immunofluorescence was conducted using a Nikon Eclipse E600 microscope with epifluorescence, and photographed with a Qimaging Exi Aqua Monochrome Digital camera.

Proximity Ligation Assay (PLA):

Experiments were conducted utilizing the Duolink In Situ Orange Kit Mouse/Rabbit (Sigma, catalog no. DUO92102) according to the manufacturer's recommendations with some modification. Briefly, U2OS cells were plated onto coverslips at 100,000 cells per well of 24-well plates and incubated overnight in a 37° C. humidified incubator. The following day, cells were infected with 17syn+ at MOI=10 as follows: virus was adsorbed, cells were washed with PBS after 1 h, and the infection allowed to proceed for 3 h post-adsorption. Cells were fixed and processed as described previously for immunofluorescence (IF). Following permeabilization and blocking, cells were incubated with primary antibodies (same antibodies and dilutions as described for IF) for 1 h at RT, washed 3×5' with PBS containing 1% BSA and 0.1% NP-40 (WDB) and incubated with the diluted PLA probes (diluted in WDB) per manufacturer's recommendation for 1 h at 37° C. Cells were washed 2×5' with Wash Buffer A (from kit) and Detection was performed by incubating cells with the Ligation reaction mix for 30' at 37° C. Cells were washed 2×2' with Wash Buffer A and Amplification was performed by incubating cells with Polymerase reaction mix for 100 min at 37° C. Cells were washed 2×10' with Wash Buffer B (from kit) and 1×10' with 0.01× Wash Buffer B. Coverslips were mounted onto slides with Pro-Long Gold mounting media containing DAPI. PLA analysis of amplification events was carried out with the aid of Nikon's NIS-Elements basic research (BR3.2) software interfaced with a Nikon Eclipse E600 microscope using edge detection and object count dialog options.

Results

Figure 2:
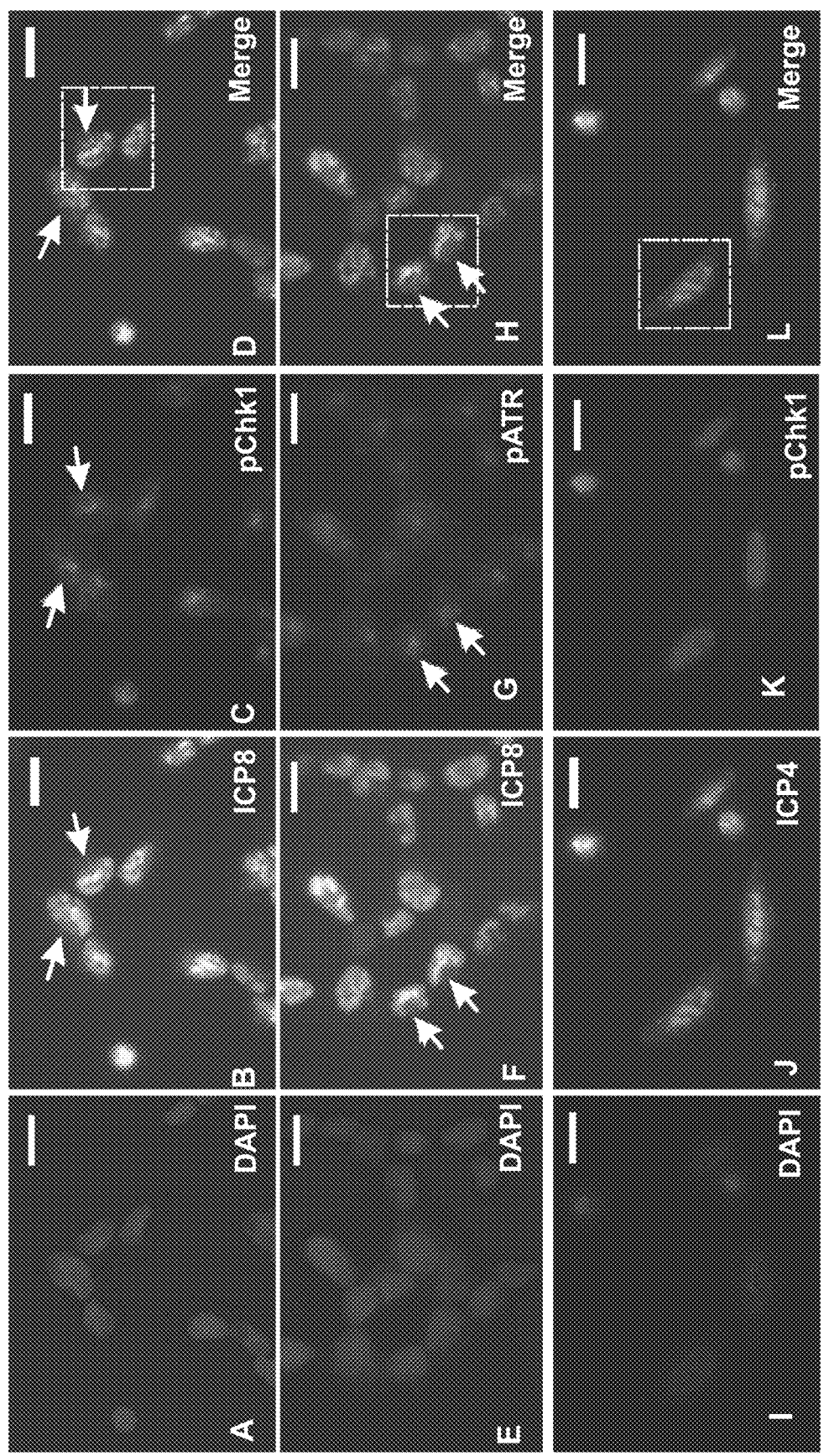
FIG. 2. Localization of pATR and pChk1 following 17+HSV-1 infection (MOI=10) of U2OS cells. Panels A-D: Localization of DAPI, ICP8, and pChk1S345 in formalin-fixed cells at 3 h.p.i. without Fc receptor block shows artifactual binding of rabbit pChk1 antibody to juxtanuclear position. Panels E-H: Localization of DAPI, ICP8, and pATRS428 in formalin-fixed cells at 3 h.p.i. without Fc receptor block shows artifactual binding of rabbit pATR antibody to juxtanuclear position. Panels I-L: Localization of DAPI, ICP4, and pChk1S345 at 4 h.p.i. with 17+HSV-1 in Fc-receptor blocked, unextracted cells. M-P: Localization of DAPI, ICP8, and pChk1S345 at 3 h.p.i. with 17+HSV-1 in Fc-receptor blocked, pre-extracted cells. Panels Q-T: Localization of DAPI, ICP8, and pATRS428 at 3 h.p.i. with 17+HSV-1 Fc-receptor blocked, pre-extracted cells. Bottom row of micrographs shows higher magnification merged images of insert boxes in Panels D, H, L & P. Scale bars=20 microns in Panels A-P, and 10 microns in bottom two rows.
Figure 2:
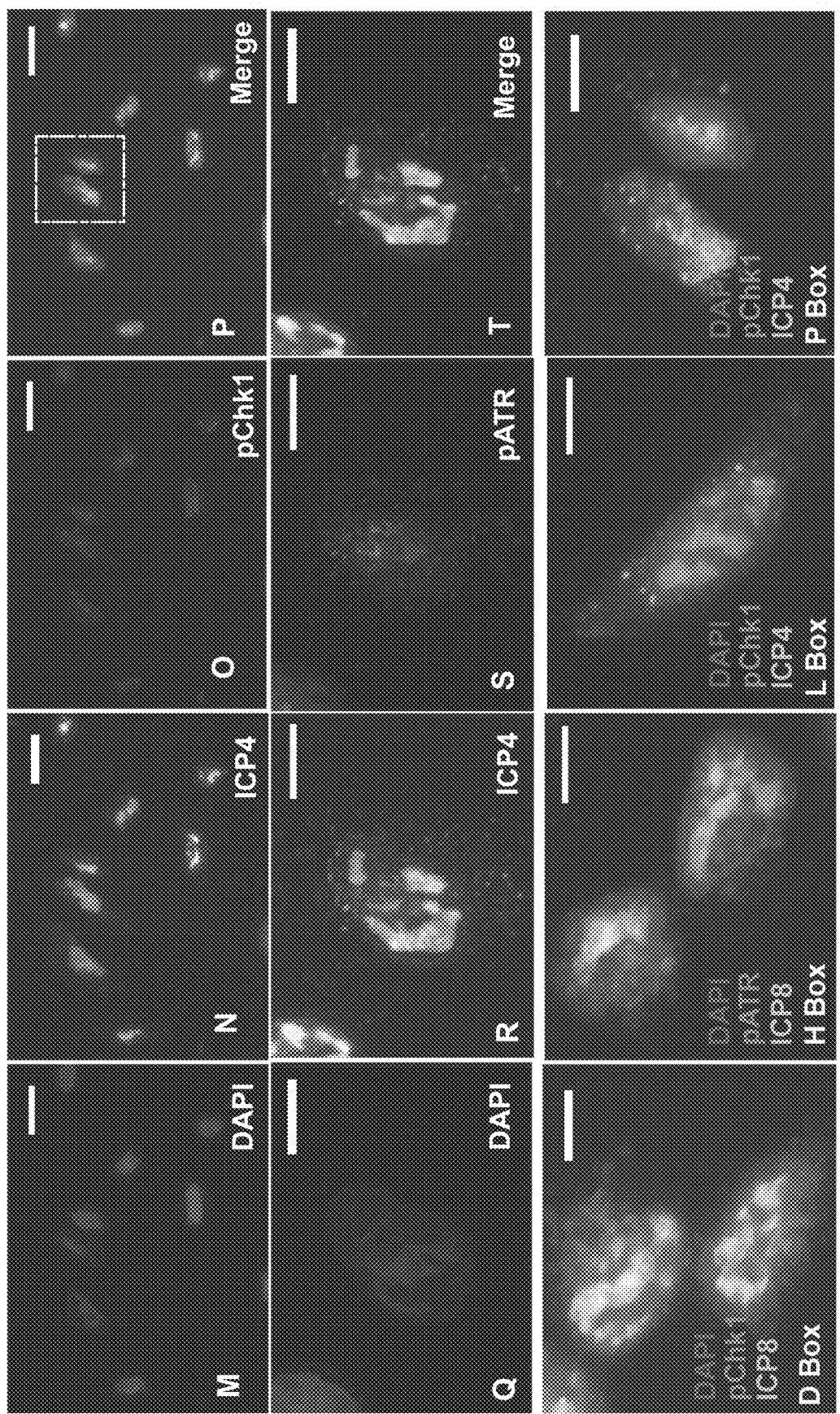

U2OS cells infected with HSV-1 (17+ strain, MOI=10) were initially examined by Western blotting (FIG. 1) and by immunofluorescence using phospho-specific antibodies (see, e.g., FIG. 2). The Western blots examined a 6 h. time course of infection. Total ATM, ATR and Chk1 levels, detected with pan-specific antibodies, did not change over the course of the experiments (FIG. 1, panels A and B). U2OS cells infected with HSV-1 (17+, MOI=10) showed a single immunoreactive band, reacting with the phospho-specific Chk1 antibody, migrating at 56 kDa and first appearing at 3 h.p.i. (FIG. 1, panel A). All subsequent time points continued to show robust Chk1 phosphorylation. Infection of Vero cells under identical conditions produced identical results (FIG. 1, panel A). ATM and ATR activation was also detected following infection. pATR levels were increased by 3 h.p.i., while pATM levels were found to be increased by 0 h.p.i., at the time of removal of HSV-1 inoculum (FIG. 1, panel B).

Figure 9:
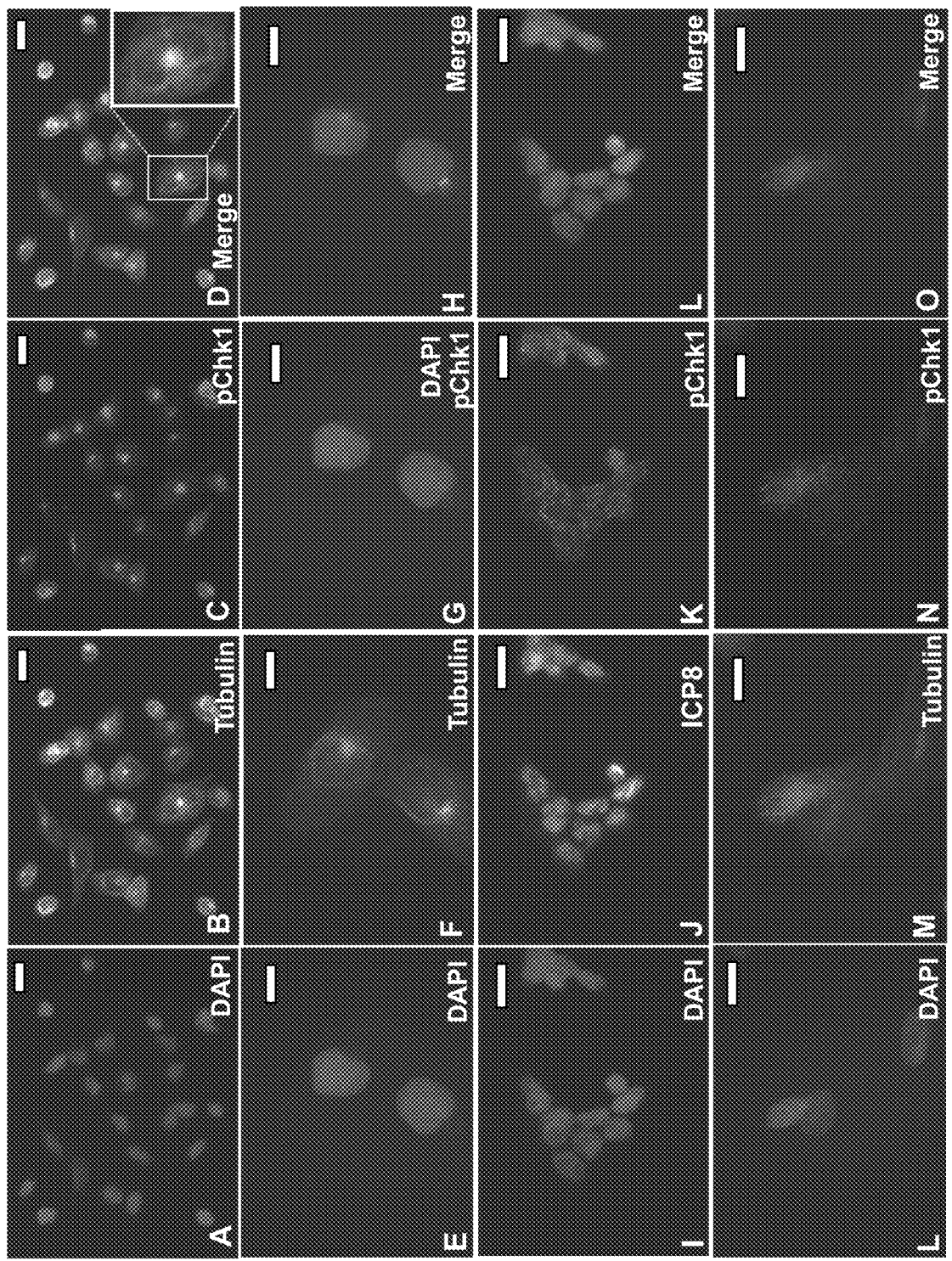
FIG. 9. Rabbit phospho-specific antibodies bind non-specifically if Fc receptor is not blocked. Initial experiments found that rabbit phospho-specific antibodies bound in the vicinity of the microtubule-organizing center (MTOC) following infection by 17+(MOI=10) of U2OS cells, and microtubule inhibition results in their cytoplasmic dispersal. A-D: Colocalization of DAPI, tubulin, and pChk1$^{S345}$ binding following 17+HSV-1 (MOI=10) at 2 h.p.i. Note that pChk1 labelling was not expected at 2 h.p.i. The box in D shows higher magnification image of pChk1 antibody binding around MTOC. Scale bars=20 microns. E-H: Higher magnification images of localization of DAPI, tubulin, and rabbit pChk1$^{S345}$ antibody binding with no Fc receptor block. Scale bars=10 microns. I-L: Localization of DAPI, ICP8, and pChk1$^{S345}$ antibody binding following HSV-1 infection (MOI=10) of U2OS cells and colchicine disruption of microtubules demonstrates that pChk1 antibody binding is dispersed throughout the cytoplasm. Scale bars=20 microns. L-O: Localization of DAPI, tubulin, and pChk1$^{S345}$ antibody binding following HSV-1 infection (MOI=10) of U2OS cells and colchicine disruption of microtubules shows dispersal of pChk1 antibody binding from the juxtanuclear position. Scale bars=20 microns.

In early experiments infected cells exhibited strong pATR and pChk1 fluorescence at 3 h.p.i. that was primarily concentrated in juxtanuclear domains (FIG. 2, panels A-H). We suspected that this finding was an artifact for several reasons. Earlier time points such as at 2 h.p.i. showed a similar result and therefore were not in agreement with Western blot time course (FIG. 9, panels A-D). The perinuclear localization of pChk1 and pATR was within the microtubule organizing center (MTOC) and disrupted by colchicine (FIG. 9). The MTOC is also the site of formation of the human cytomegalovirus (CMV) "assembly compartment," which was previously shown to especially bind rabbit IgG antibodies (62) due to the presence of CMV encoded Fc receptor-like protein (63) causing spurious results.

Figure 7:
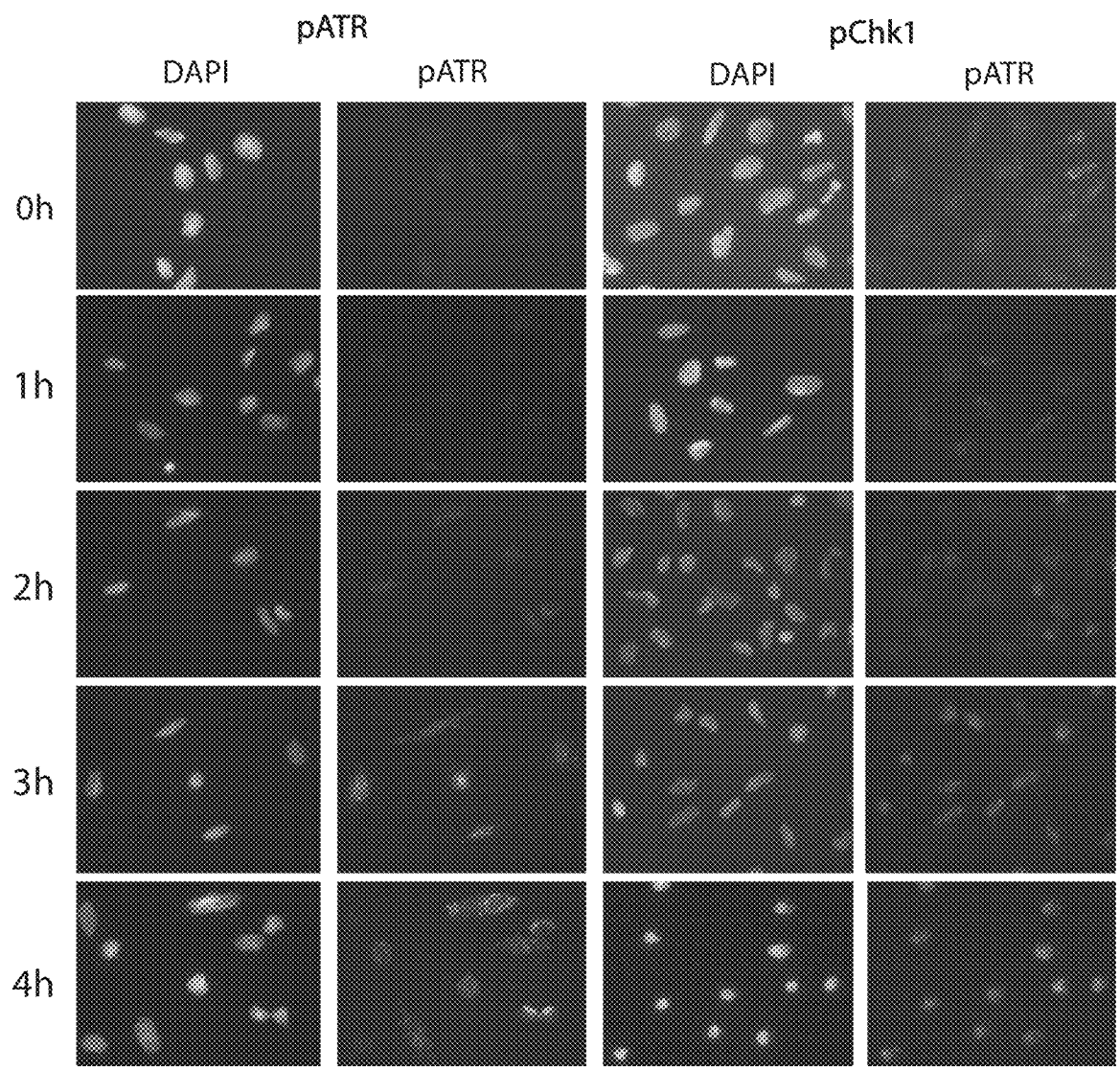
FIG. 7. Immunofluorescence time course after blocking non-specific binding with Fc receptor blocking reagent shows activation of ATR and Chk1 following 17+HSV-1 infection (MOI=10), which is consistent with Western blot time course (FIG. 1).

We therefore optimized our immunofluorescence protocol to include an Fc receptor blocking step and, in some cases, a modification of a widely used procedure for studying DDR dynamics by in situ fractionation followed by preservation with Streck's fixative (64). When applied to a time course of HSV-1 infected cells, the results faithfully reproduced the kinetics of ATR and Chk1 activation seen in Western blots (FIG. 7). Both pChk1 (FIG. 2, panels I-L & M-P) and pATR (FIG. 2, panels Q-T) were activated and localized to the nucleus. HSV-1 replication centers were well established by 4 h.p.i., and foci of both pChk1 (FIG. 2, panels I-L & M-P) and pATR (FIG. 2, panels Q-T) and were found associated mainly with the periphery of these structures within the nucleus. The pChk1 fluorescence was found primarily in discreet nuclear puncta (see FIG. 2, panels L and P), while the pATR fluorescence was both punctate and diffuse (FIG. 2, panels Q-T). The in situ fractionation procedure had the expected effect of reducing total nuclear labeling of pATR and pChk1 with extracted cells, while preserving punctate foci associated with the periphery of replication centers. For example, compare unextracted cells (FIG. 2, panels I-L; and L-box) to extracted cells (FIG. 2, panels M-T; and P-box). The foci surviving the in situ extraction procedure represent insoluble, chromatin-associated DDR complexes.

Example 2: Activated ATR and Chk1 Interact with ICP4, ICP0, and Tubulin, but not with ICP8 and ICP27

Results

Figure 3:
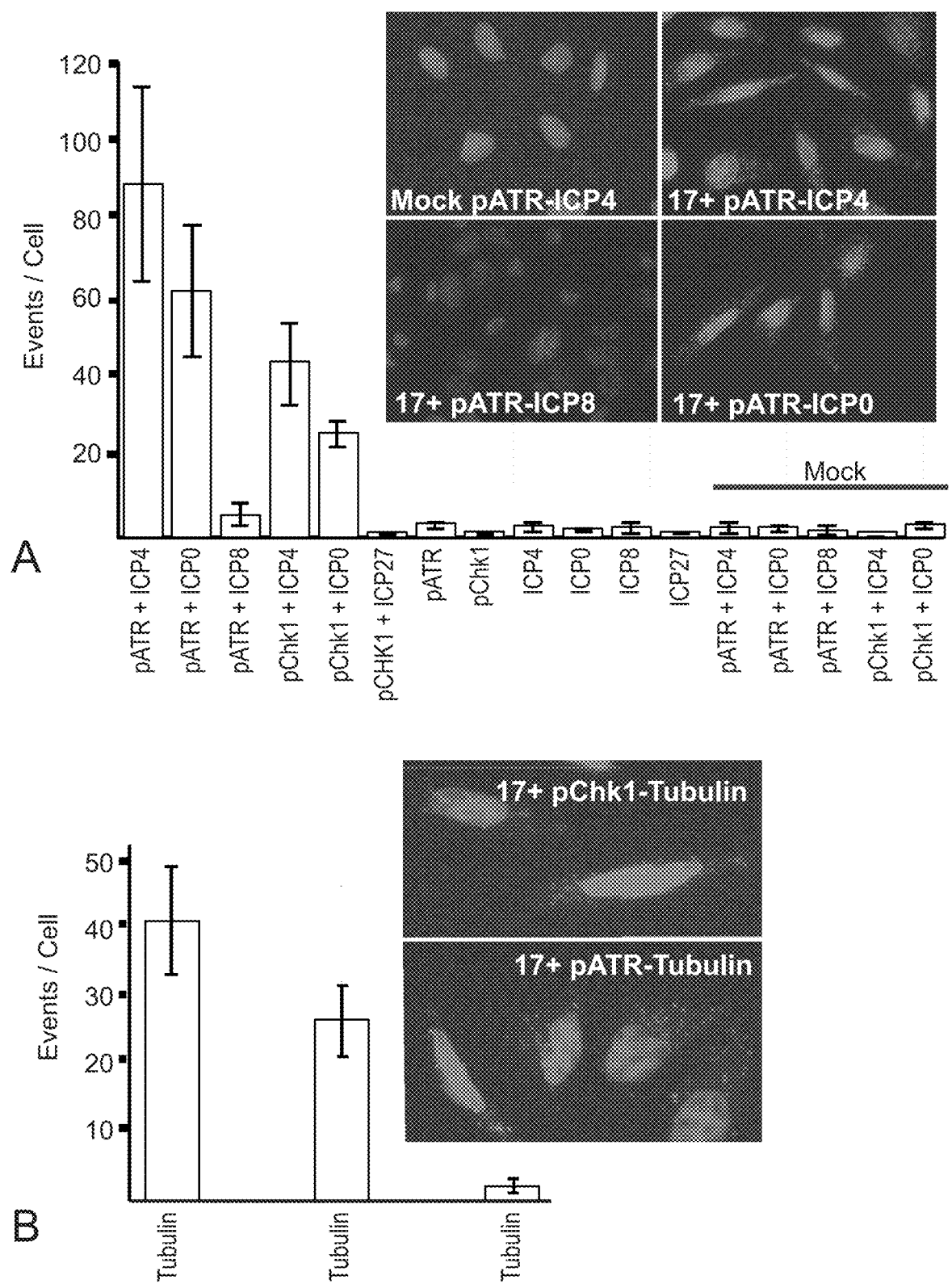
FIG. 3. Proximity Ligation Assay (PLA) demonstrates the close association of pATR and pChk1 with ICP0, ICP4 and tubulin at 3 h.p.i of U2OS cells with 17+HSV-1. Panel A. Bar graph shows the number of positive amplification events per cell for phospho-ATR(S428) or phospho-Chk1(S345) interaction with the indicated proteins. No significant interactions were found in mock-infected cells, while infected cells showed significant pATR and PChk1 interactions with ICP0 and ICP4, but not with ICP8 or ICP27. PLA for individual proteins established background levels. Insert micrographs show representative images of the indicated PLA results. Panel B. Bar graph shows the number of positive amplification events per cell for phospho-ATR (S428) or phospho-Chk1(S345) interaction with tubulin. PLA for tubulin alone was negative. Insert micrographs show representative images of the indicated PLA results. Scale bars=10 microns.
Figure 5:
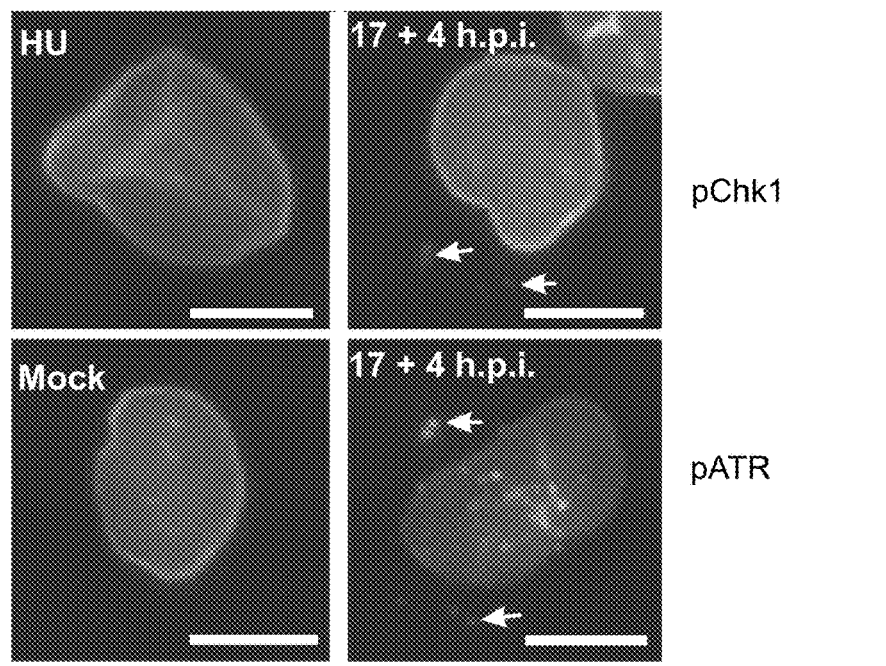
FIG. 5. Activated Chk1 and ATR are found in the nucleus and also in the cytoplasm where they sometimes co-localize with ICP4.
Figure 5:
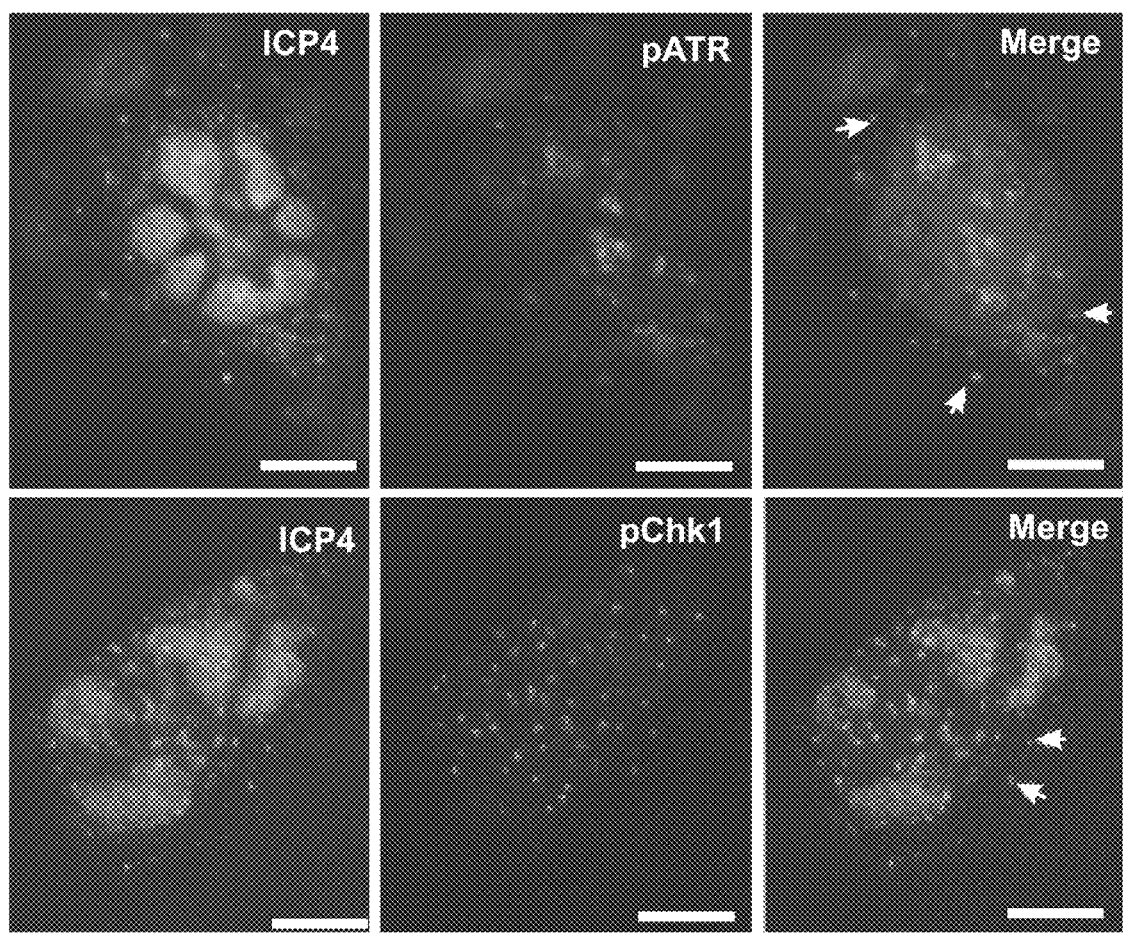
Figure 5:
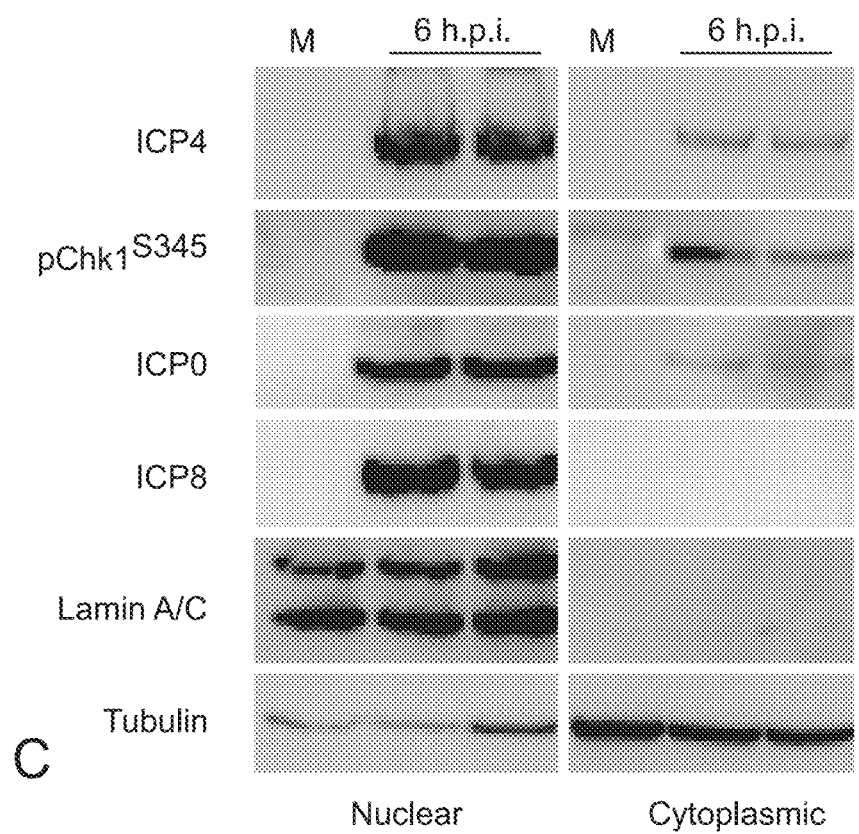

Colocalization of pATR and pChk1 with ICP4 and ICP0 suggested that these proteins may be exist together within a complex. This idea was tested using a Proximity Ligation Assay (PLA), which allows localization of the interaction of native protein pairs within a maximum distance of approximately 30 nM (32). PLA was initially used to explore the interaction of pATR with ICP4 and ICP0 in U2OS cells at 3 h.p.i. In both cases significant, bright signals were detected throughout the cytoplasm with some interaction foci also detected within the nuclei (FIG. 3, panel A). PLA was negative for interaction between pATR and either ICP8 or ICP27 (FIG. 3, panel A). PLA conducted for the individual proteins were all negative, as were all PLA conducted following mock infection. PLA was next conducted in an identical fashion for pChk1. These tests resulted in nearly identical results as pATR except that the total number and brightness of PLA signals were lower (FIG. 3, panel A). PLA for individual proteins and mock-infected samples were again negative (FIG. 3, panel A). The PLA signal when detected for either ICP4 or ICP0 was distributed widely in the cell, but more prominent in the cytoplasm. The results showed agreement with the cell fractionation results that ICP4 and ICP0, but not ICP8, are found in the cytoplasm following infection (FIG. 5, panel C).

The interaction of pATR and pChk1 with tubulin was tested next. Both activated enzymes gave strong positive PLA signals for tubulin interaction, while tubulin alone was negative (FIG. 3, panel B). Again, as for interactions detected for ICP4 and ICP0, the PLA amplification events were distributed primarily throughout the cytoplasm. Together these results indicate that both pATR and pChk1 are forming complexes with both ICP4 and ICP0, and these complexes are found in close association with microtubules.

Co-localization of pChk1 and pATR with Lamin A/B (FIG. 5, panel A) revealed significant activation of both proteins within the nucleus. In addition, significant pATR and pChk1 immuno-labelling occurred within the cytoplasm following HSV-1 infection compared to mock infected cells or cells in which ATR and Chk1 are activated by HU (FIG. 5, panel A). Co-localization of pATR and pChk1 with ICP4 showed significant nuclear accumulation of these proteins where they appear to associate with replication centers, often on the periphery (FIG. 5, panel B). Both pATR and pChk1 were also often are seen to co-localize with ICP4 within the cytoplasm (FIG. 5, panel B). ICP0 also co-localized with ICP0 (data not shown). To confirm the cytoplasmic distribution of proteins we fractionated mock infected cells, as well as cells infected for 6 h. with 17+(MOI=10) and subjected the fractions to Western blotting (FIG. 5, panel C). The results showed that cytoplasmic and nuclear fractions were cleanly separated with nuclear lamins and tubulin separating into the appropriate fractions. Most pChk1 separated with the nuclear fraction, but a significant amount of pChk1 was also detected in the cytoplasmic fraction of infected cells, but not mock-infected cells. In agreement with their immunofluorescence localization, a similar result was obtained for ICP4 and ICP0, but not ICP8, which was only detected in the nuclear fraction (FIG. 5, panel C).

Figure 6:
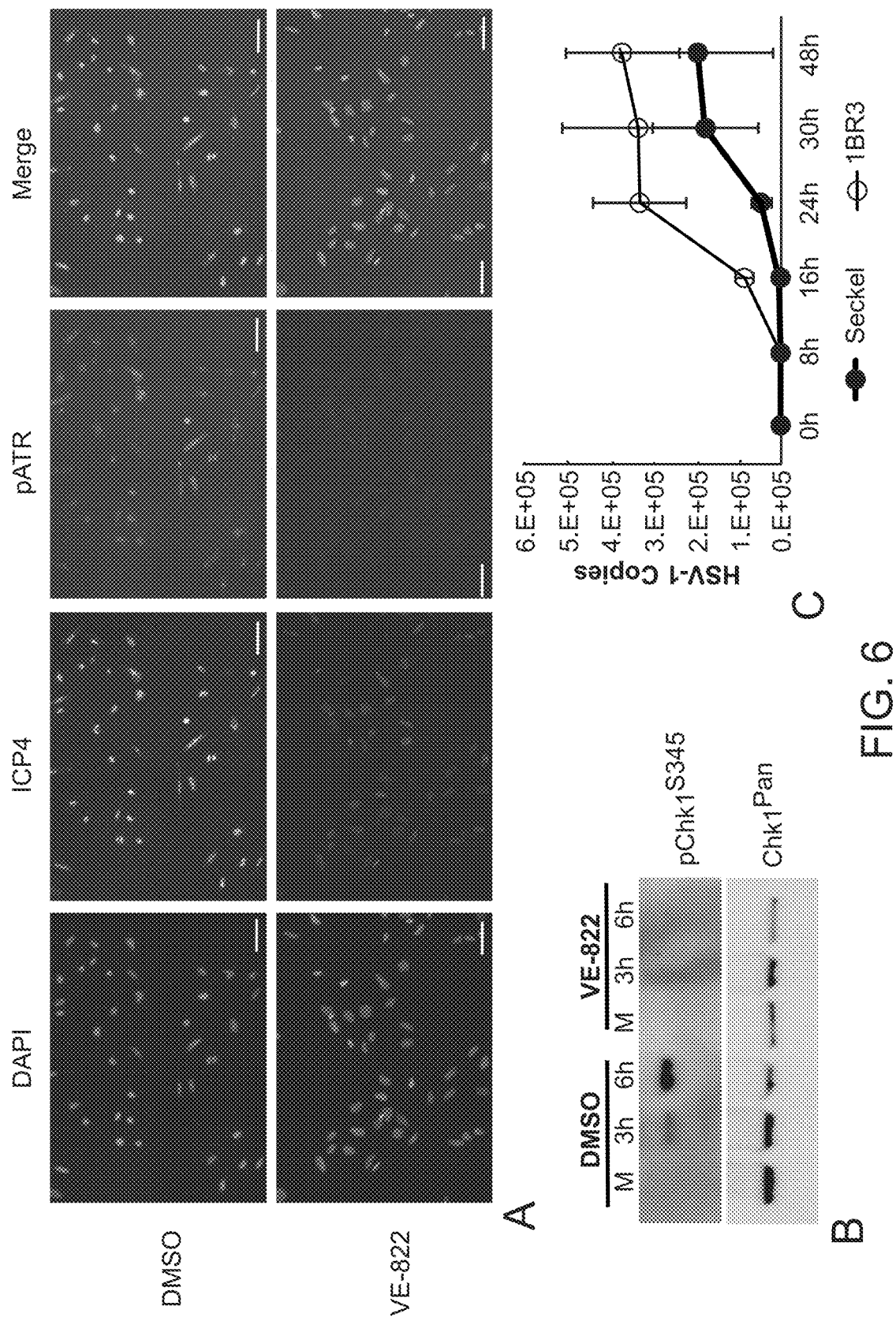
FIG. 6. Inhibition of ATR with VE-822 blocks activation of ATR and Chk-1, while HSV-1 replication is deficient in Seckel patient fibroblasts hypomorphic for ATR.

The specific ATR kinase VE-822 was next used to examine ATR/Chk1 activation (FIG. 6). Cells receiving vehicle (0.1% DMSO) or ATR inhibitor (10 μM) were infected with HSV-1 (17+, MOI=10) and examined by Western blotting. VE-822 blocked ATR activation as observed by immunofluorescence (FIG. 6, panel A), while Chk1 activation was also blocked as observed in Western blots (FIG. 6, panel B). Interestingly, this series of experiments also showed that ATR inhibition by VE-822 blocked expression of ICP4 (FIG. 6, Panel A) and ICP8 (data not shown) suggesting ATR kinase activity is required for viral fitness and viral DNA replication. The production of HSV-1 genomes following infection (MOI=0.1) of normal fibroblasts and fibroblasts derived from a Seckel syndrome patient was therefore examined Seckel fibroblasts carry an ATR hypomorphic mutation resulting in impaired ATR function (28). HSV-1 replication was depressed in the ATR-deficient cells relative to the normal patient fibroblasts throughout the 48 h. time course (FIG. 6, panel C).

Example 3: ATR and Chk1 Activity is Required for Efficient HSV-1 Replication

Results

Figure 4:
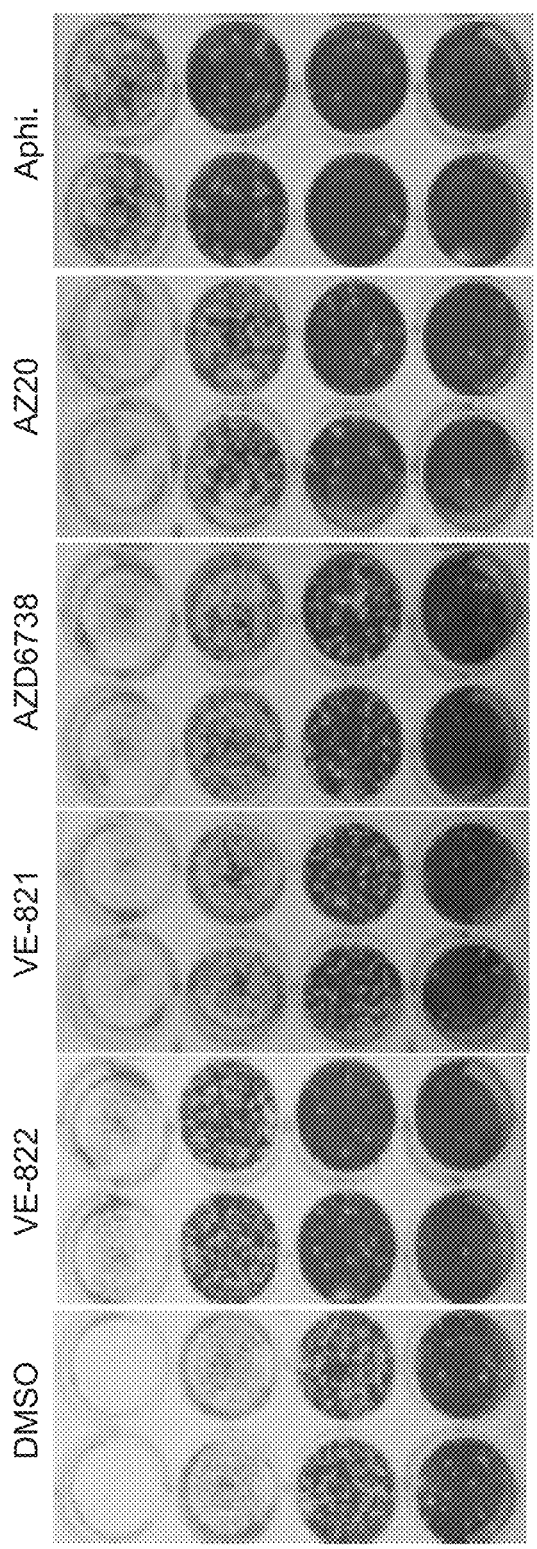
FIG. 4. Inhibition of either ATR or Chk1 kinase activity significantly inhibits HSV-1 replication and virus production. Panel A, Representative photos of HSV-1 titer plates show the effects of inhibitors on virus production. Panel B. Quantification of HSV-1 PFU following inhibitor treatment shows that all ATR and Chk1 inhibitors tested, and the control polymerase inhibitor aphidicolin, significantly impact virus production. Inhibitors against ATM, Chk2, or DNA-PK were not found to significantly inhibit virus production. Asterisk (*) indicates statistical significance (Student's t-test): $p \leq 0.005$ in all cases except for PF477736 where p=0.006. Panel C. Q-PCR measurements of HSV-1 genome copies show good agreement with the viral titer assays.
Figure 4:
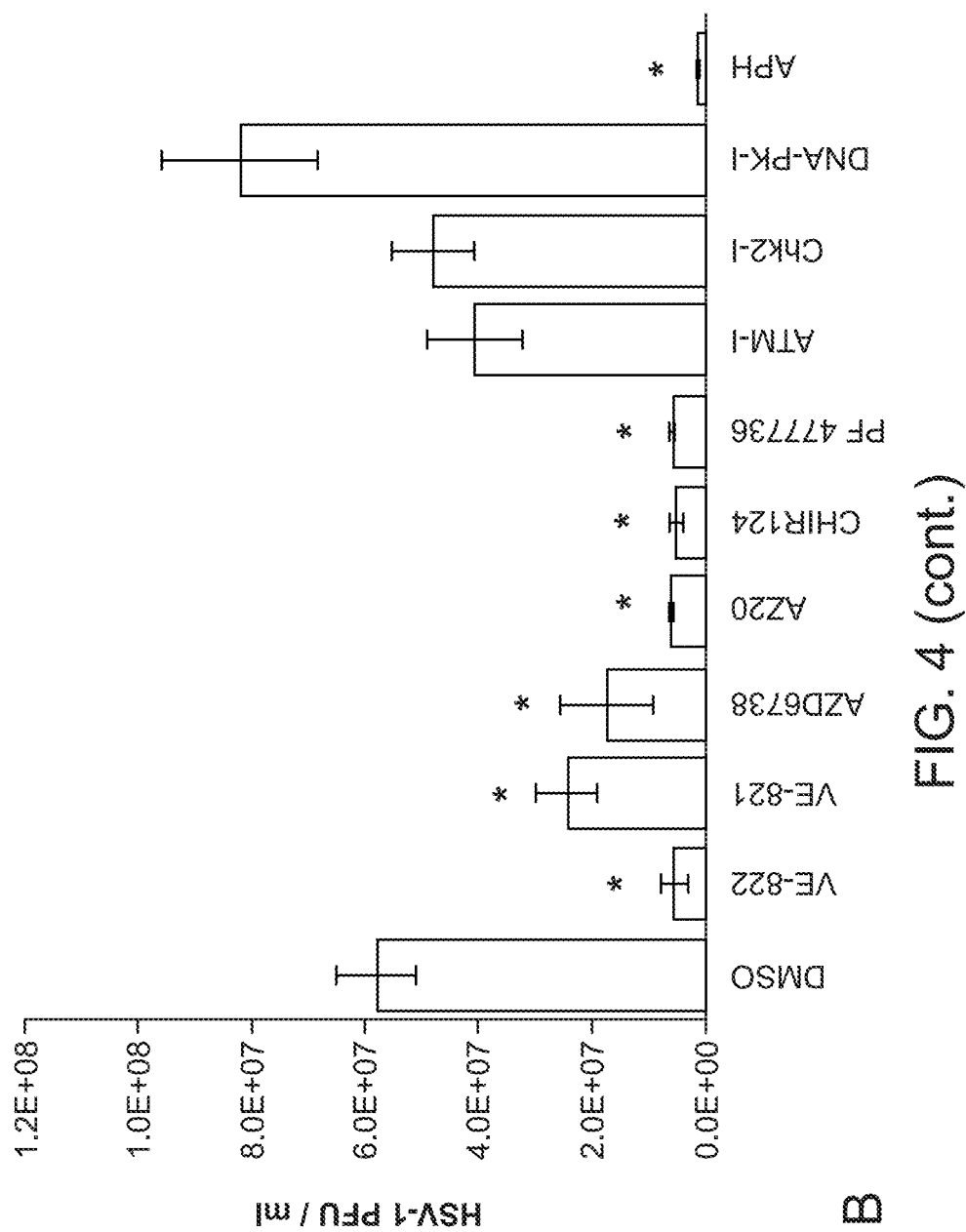
Figure 4:
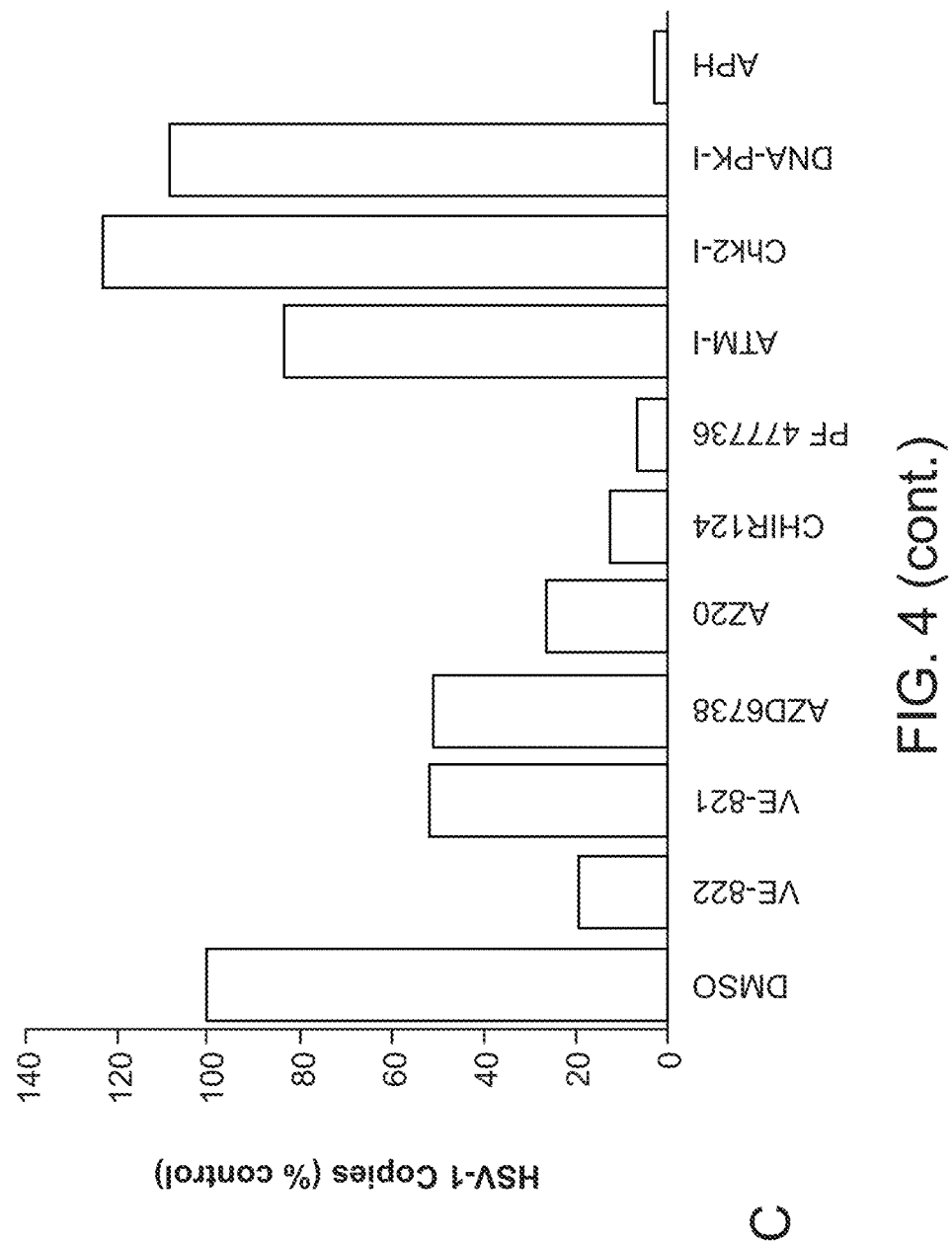
Figure 8:
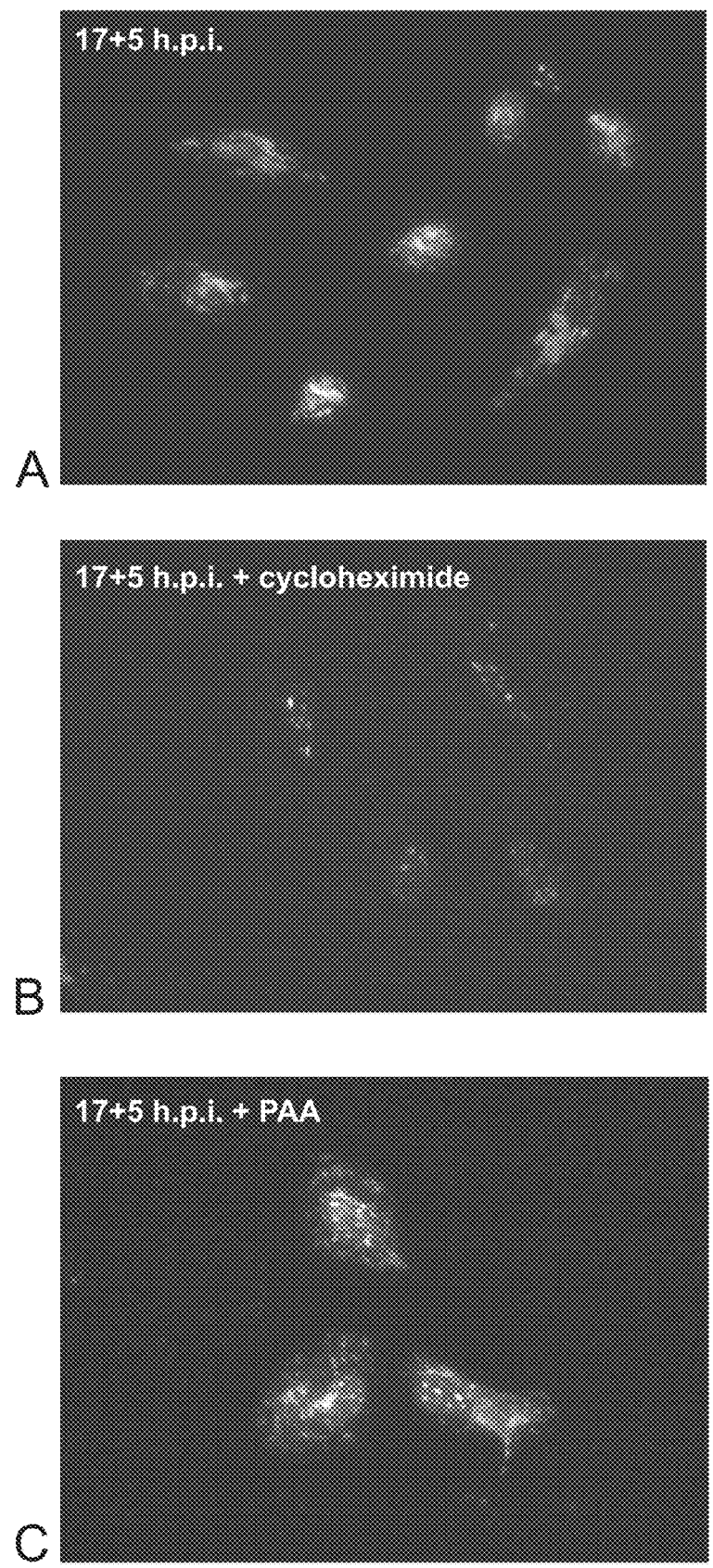
FIG. 8. Merged images of DAPI, ICP4, and pATR following.

Inhibition of protein synthesis with cycloheximide completely blocked ATR activation, while the viral polymerase inhibitor PAA partially suppressed ATR activation (FIG. 8). These results suggested that the incoming viral inoculum was not responsible for ATR activation, and that viral DNA synthesis, while not required for ATR activation, may contribute to amplification ATR activation. We next asked a whether pharmacological inhibition of ATR or Chk1 kinase has antiviral effects upon HSV-1 replication. U2OS cells infected with 17+HSV-1 (MOI=0.1) were treated with one of four chemically distinct ATR inhibitors (VE-822, VE-821, AZD-6738, and AZ20), or 2 unique Chk1 inhibitors (Chir124 and PF477736), or inhibitors of ATM, Chk2, or DNA-PK (FIG. 4). Following the treatment infected cells were harvested to conduct viral titer assays and for Q-PCR to quantify HSV-1 genome copies. All ATR and Chk1 inhibitors, as well as the positive control aphidicolin that was expected to inhibit both viral and cell DNA replication (34) were determined to significantly inhibit viral titers (P=<0.01) (FIG. 4, panels A&B). Inhibition of ATM, Chk2, and DNA-PK, on the other hand, modestly suppressed viral titers but not significantly (FIG. 4, panels A&B). The measurement of viral genome copies, measured by Q-PCR, reflected and confirmed the viral titer results (FIG. 4, panel C).

ICP0, ICP4, and ICP27 are IE phosphoproteins with the greatest effects upon HSV-1 gene expression and growth (1, 19, 35, 36). All three proteins have consensus Chk1 phosphorylation sites but no ATR sites. Interestingly, ICP8, an IE ssDNA binding protein that organizes the earliest stages of HSV-1 replication (37-39), has 3 ATR consensus sites and one Chk1 site. One ATR site exists within the C-terminal 60 amino acid region that is required for ICP8 filament assembly and cooperative ssDNA binding (40, 41), immediately adjacent to a short sequence apparently required for ICP8 self-interactions (42). Numerous other HSV-1 proteins with central roles in viral DNA replication also possess multiple ATR and Chk1 consensus sites.

We show here using a variety of evidence that both ATR and Chk1 are rapidly activated following HSV-1 infection. Both ATR and Chk1 are rapidly phosphorylated following infection and pharmacological inhibition of ATR, but not ATM, blocks Chk1 phosphorylation, blocks formation of viral replication centers, and has a negative impact upon viral replication. We can only speculate why the previous Western blotting studies did not detect HSV-1-dependent Chk1 phosphorylation. Previous studies of ATR and Chk1 localization during HSV-1 infection utilized pan-specific antibodies to examine nuclear localization. We observe little alteration in localization of the ATR or Chk1 protein pool during infection using pan-specific antibodies, but see dramatic changes in localization of phosphorylated proteins with phospho-specific antibodies. These results indicate that the activated ATR and Chk1 moieties make up a relatively small portion of their respective protein pools.

Viral DNA replication is required for activation of the ATR pathway following infection. Incoming viral genomes at the earliest stages of HSV-1 infection are linear DNAs with ends, nicks, and gaps that might be expected of to activate DDR pathways (43-45). For this reason we tested whether Vero cells activate ATR following infection with the replication-incompetent KD6 mutant. No evidence of Chk1 activation was noted in Vero cells although Chk1 was clearly activated following KD6 infection of permissive Vero cell line K5, and activation in these cells was blocked by the protein synthesis inhibitor cycloheximide. These results indicate that ICP4-dependent viral DNA replication, not the inoculum or the incoming viral genomes, is required to activate the ATR pathway.

Both pATR and pChk1 were found to interact by PLA in close proximity with both ICP4 and ICP0 predominantly in the cytoplasm. While it cannot at present be ruled out that these interactions represent individual protein-protein associations, we believe the simplest explanation is that the four proteins are interacting with each other within a large, multiprotein complex. The interaction of ICP4 and ICP0 has long been recognized as important for activation of E and L gene expression. ICP0 was first identified based upon its ability to cooperate with ICP4 to promote viral mRNA synthesis (50, 51). Studies of the ability of ICP0-viruses to replicate at low versus high MOIs led to the concept that ICP0 inactivates a repressor of HSV gene expression (52-54). Other studies have shown that the two proteins are able to physically interact (55, 56).

ATR and Chk1 are activated shortly after infection of multiple cell lines by HSV-1 strains 17+, KOS, McKrae, or McIntyre. The pathway appears to be activated by events of early gene expression. pATR and pChk1 are found in the nucleus within viral replication centers or on their periphery. Both pATR and pChk1 are also found in the cytoplasm during early stages of infection where they directly interact with ICP4 and ICP0. The specific ATR inhibitor VE-822 blocks activation of both ATR and Chk1 during infection. It also blocks maturation of replication centers during infection by blocking expression of both ICP4 and ICP8. Viral replication and production is significantly attenuated by treatment with multiple, chemically-distinct inhibitors of ATR and Chk1, but not inhibitors of ATM or Chk2. HSV-1 replication is also impaired in Seckel patient fibroblasts that are hypomorphic ATR. Together these findings demonstrate that HSV-1 activates pATR and pChk1 during infection, and that the activated kinases significantly contribute to HSV-1 replication fitness during early stages of infection.

Significant precedence exists for the cytoplasmic localization and function of activated ATR and Chk1. ATR regulates hundreds of down-stream targets, including anti-apoptotic mitochondrial elements, and its distribution in the cytoplasm following DNA damage is well documented (65). Likewise, Chk1 has nuclear export sequences and is mobilized to control cytoplasmic targets following DNA damage (66). Precedence also exists for exploitation of these DDR elements in the cytoplasm by viruses. Vaccinia, a poxvirus that replicates exclusively in the cytoplasm, activates cytoplasmic ATR, ATM, and DNA-PK, and utilizes ATR and Chk1 to promote viral genome replication (67, 68). We show that activated ATR and Chk1 appear in the cytoplasm at early stages of HSV-1 infection where they associate with ICP4 and ICP0. To the best of our knowledge, this is the first report of the cytoplasmic localization and association of activated ATR and Chk1 with ICP4 and ICP0 during HSV-1 infection. Cell fractionation, immunofluorescence co-localization, and PLA data all support this novel finding. We are at present unsure of what role this cytoplasmic association plays in the early stages of HSV-1 infection, but our data clearly show that ATR and Chk1 kinase activities are playing important roles in viral replication fitness.

Incoming viral genomes at the earliest stages of HSV-1 infection are linear DNAs with ends, nicks, and gaps that might be expected of to activate DDR pathways (43-45). However, the complete suppression of ATR and Chk1 activation by cycloheximide indicates that new protein synthesis is required for ATR activation, and suggests that incoming viral genomes are not the cause of activation. Since the ATR pathway is also activated at early times during acute infection in the presence of PAA, a viral polymerase inhibitor, we hypothesize that early gene expression rather than viral DNA replication is an important initial event resulting in ATR activation. The partial suppression of ATR activation by PAA suggests that viral DNA replication may contribute to the amplification of the ATR signaling cascade.

Activated ATR and Chk1 are found within the nucleus associated with the periphery of developing viral replication centers after 3 h. of HSV-1 infection. Pharmacological inhibition of ATR dramatically halts viral replication center growth and maturation. The data clearly demonstrate that ATR and Chk1 are robustly activated, and that ATR and Chk1 kinase activities are required for early HSV-1 fitness and replication. But the data are inconsistent with previous reports that concluded ATR is not activated during HSV-1 infection (17, 22), and that ATR is purposely inactivated by HSV-1 infection (23, 24). To the best of our knowledge, pATR or pChk1 localization by immunological techniques using phospho-specific antibodies were not pursued in these studies. Previous reports of ATR inactivation by HSV-1 also rested heavily upon the observation that HSV-1 infection blocks phosphorylation of the nuclear ATR target RPA (24). Perhaps one function of the association of ICP4 and ICP0 with activated ATR and Chk1 that we report here is to redirect their kinase activity away from cellular targets to viral targets that promote viral DNA replication. Whether this notion eventually proves true or not, our data strongly attests to the need at least for re-evaluation of the hypothesis that HSV-1 inactivates ATR.

Multiple ATR and Chk1 inhibitors show potent antiviral effects against HSV-1 when used at concentrations that are reported to significantly inhibit their target protein and spare closely related kinases such as ATM and Chk2. These findings show that ATR and Chk1 kinase activities are utilized by HSV-1 to promote important aspects of viral gene expression and replication. Consistent with this is the observation that ATR inhibition: 1) inhibits expression of early genes (such as ICP4 and ICP8); 2) blocks the maturation of viral nuclear replication centers; and 3) suppresses viral growth as measured by Q-PCR or and plaque assay. While the mechanism by which ATR pathway activation enhances HSV infection is currently not clear, we hypothesize it is through down-stream effects on viral and/or host processes. Perhaps ICP4 and ICP0 act to re-direct ATR and Chk1 phosphorylation away from host targets to HSV replication proteins. It should will be useful to identify those targets of ATR and Chk1 phosphorylation that are required to maintain early viral gene expression, replication, and fitness. Importantly, the understanding that ATR and Chk1 are activated by HSV-1 to promote viral fitness will enable future studies designed to understand this important process and to perhaps design new therapeutic approaches.

REFERENCES

1. Roizman B & Knipe D M (2001) Herpes Simplex Viruses and Their Replication. Fields Virology, eds Knipe D M & Howley P M (Lippencott Williams & Wilkins, Philadelphia), 4th Ed Vol 2, pp 2399-2457.
2. Weller S K & Coen D M (2012) Herpes Simplex Viruses: Mechanisms of DNA Replication. Cold Spring Harbor Perspectives in Biology 4(9).
3. Weitzman M D, Lilley C E, & Chaurushiya M S (2010) Genomes in Conflict: Maintaining Genome Integrity During Virus Infection. Annual Review of Microbiology, Vol 64, 2010, Annual Review of Microbiology, eds Gottesman S & Harwood C S), Vol 64, pp 61-81.
4. Turnell A S & Grand R J (2012) DNA viruses and the cellular DNA-damage response. J Gen Virol 93(Pt 10): 2076-2097.
5. Luftig M (2014) Viruses and the DNA Damage Response: Activation and Antagonism. Annual Review of Virology 1:20.
6. Harper J W & Elledge S J (2007) The DNA damage response: ten years after. Mol Cell 28(5):739-745.
7. Stracker T H, Usui T, & Petrini J H (2009) Taking the time to make important decisions: the checkpoint effector kinases Chk1 and Chk2 and the DNA damage response. DNA Repair (Amst) 8(9):1047-1054.
8. Marechal A & Zou L (2013) DNA Damage Sensing by the ATM and ATR Kinases. Cold Spring Harbor Perspectives in Biology 5(9):17.
9. Brown E J & Baltimore D (2000) ATR disruption leads to chromosomal fragmentation and early embryonic lethality. Genes Dev 14(4):397-402.
10. Brown E J & Baltimore D (2003) Essential and dispensable roles of ATR in cell cycle arrest and genome maintenance. Genes Dev 17(5):615-628.
11. Cortez D, Guntuku S, Qin J, & Elledge S J (2001) ATR and ATRIP: Partners in checkpoint signaling. Science 294(5547):1713-1716.
12. Wang H Y, Wang H C, Powell S N, Iliakis G, & Wang Y (2004) ATR affecting cell radiosensitivity is dependent on homologous recombination repair but independent of nonhomologous end joining. Cancer Res 64(19):7139-7143.
13. You Z, et al. (2009) CTiP Links DNA Double-Strand Break Sensing to Resection. Mol Cell 36(6):954-969.
14. Tomimatsu N, et al. (2012) Exo1 plays a major role in DNA end resection in humans and influences double-strand break repair and damage signaling decisions. DNA Repair (Amst) 11(4):441-448.
15. Peng G, et al. (2012) Human Nuclease/Helicase DNA2 Alleviates Replication Stress by Promoting DNA End Resection. Cancer Res 72(11):2802-2813.
16. Smith S & Weller S K (2015) HSV-I and the cellular DNA damage response. Future Virol 10(4):383-397.
17. Lees-Miller S P, et al. (1996) Attenuation of DNA-dependent protein kinase activity and its catalytic subunit by the herpes simplex virus type 1 transactivator ICP0. J Virol 70(11):7471-7477.
18. Parkinson J, Lees-Miller S P, & Everett R D (1999) Herpes simplex virus type 1 immediate-early protein Vmw110 induces the proteasome-dependent degradation of the catalytic subunit of DNA-dependent protein kinase. J Virol 73(1):650-657.
19. Boutell C & Everett R D (2013) Regulation of alpha-herpesvirus infections by the ICP0 family of proteins. Journal of General Virology 94:465-481.
20. Lilley C E, Carson Conn., Muotri Ark., Gage F H, & Weitzman M D (2005) DNA repair proteins affect the lifecycle of herpes simplex virus 1. Proc Natl Acad Sci USA 102(16):5844-5849.
21. Shirata N, et al. (2005) Activation of ataxia telangiectasia-mutated DNA damage checkpoint signal transduction elicited by herpes simplex virus infection. Journal of Biological Chemistry 280(34):30336-30341.
22. Wilkinson D E & Weller S K (2004) Recruitment of cellular recombination and repair proteins to sites of herpes simplex virus type 1 DNA replication is dependent on the composition of viral proteins within prereplicative sites and correlates with the induction of the DNA damage response. J Virol 78(9):4783-4796.
23. Lilley C E, et al. (2010) A viral E3 ligase targets RNF8 and RNF168 to control histone ubiquitination and DNA damage responses. Embo Journal 29(5):943-955.

24. Lo Piano A, Martinez-Jimenez M I, Zecchi L, & Ayora S (2011) Recombination-dependent concatemeric viral DNA replication. Virus Res 160(1-2):1-14.
25. Mohni K N, Dee A R, Smith S, Schumacher A J, & Weller S K (2013) Efficient Herpes Simplex Virus 1 Replication Requires Cellular ATR Pathway Proteins. J Virol 87(1):531-542.
26. Wilkinson D E & Weller S K (2006) Herpes simplex virus type I disrupts the ATR-dependent DNA-damage response during lytic infection. J Cell Sci 119(13):2695-2703.
27. Wilkinson D E & Weller S K (2005) Inhibition of the herpes simplex virus type 1 DNA polymerase induces hyperphosphorylation of replication protein a and its accumulation at S-phase-specific sites of DNA damage during infection. J Virol 79(11):7162-7171.
28. Mohni K N, Smith S, Dee A R, Schumacher A J, & Weller S K (2013) Herpes Simplex Virus Type 1 Single Strand DNA Binding Protein and Helicase/Primase Complex Disable Cellular ATR Signaling. PLoS Pathog 9(10).
29. Mohni K N, Livingston C M, Cortez D, & Weller S K (2010) ATR and ATRIP Are Recruited to Herpes Simplex Virus Type 1 Replication Compartments Even though ATR Signaling Is Disabled. J Virol 84(23):12152-12164.
30. Botting C, Lu X, & Triezenberg S J (2016) H2AX phosphorylation and DNA damage kinase activity are dispensable for herpes simplex virus replication. Virol J 13:11.
31. Johnston J A, Ward C L, & Kopito R R (1998) Aggresomes: A cellular response to misfolded proteins. Journal of Cell Biology 143(7):1883-1898.
32. Soderberg O, et al. (2006) Direct observation of individual endogenous protein complexes in situ by proximity ligation. Nature Methods 3(12):995-1000.
33. Dobson A T, Margolis T P, Sedarati F, Stevens J G, & Feldman L T (1990) A LATENT, NONPATHOGENIC HSV-1-DERIVED VECTOR STABLY EXPRESSES BETA-GALACTOSIDASE IN MOUSE NEURONS. Neuron 5(3):353-360.
34. Larsson A, Wraak M, & Oberg B (1983) EFFECT OF APHIDICOLIN ON DNA-SYNTHESIS IN HSV-1 INFECTED AND UNINFECTED VERO CELLS. Antiviral Res 3(2):87-91.
35. Deluca N A, McCarthy A M, & Schaffer P A (1985) ISOLATION AND CHARACTERIZATION OF DELETION MUTANTS OF HERPES-SIMPLEX VIRUS TYPE-1 IN THE GENE ENCODING IMMEDIATE-EARLY REGULATORY PROTEIN-ICP4. J Virol 56(2):558-570.
36. Roizman B, Gu H D, & Mandel G (2005) The first 30 minutes in the life of a virus-unREST in the nucleus. Cell Cycle 4(8):1019-1021.
37. Kops A D & Knipe D M (1988) FORMATION OF DNA-REPLICATION STRUCTURES IN HERPES-VIRUS INFECTED-CELLS REQUIRES A VIRAL-DNA BINDING-PROTEIN. Cell 55(5):857-868.
38. Bush M, et al. (1991) CORRECT INTRANUCLEAR LOCALIZATION OF HERPES-SIMPLEX VIRUS-DNA POLYMERASE REQUIRES THE VIRAL ICP8 DNA-BINDING PROTEIN. J Virol 65(3):1082-1089.
39. McNamee E E, Taylor T J, & Knipe D M (2000) A dominant-negative herpesvirus protein inhibits intranuclear targeting of viral proteins: Effects on DNA replication and late gene expression. J Virol 74(21):10122-10131.
40. Mapelli M, Muhleisen M, Persico G, van der Zandt H, & Tucker P A (2000) The 60-residue C-terminal region of the single-stranded DNA binding protein of herpes simplex virus type 1 is required for cooperative DNA binding. J Virol 74(19):8812-8822.
41. Mapelli M, Panjikar S, & Tucker P A (2005) The crystal structure of the herpes simplex virus 1 ssDNA-binding protein suggests the structural basis for flexible, cooperative single-stranded DNA binding. Journal of Biological Chemistry 280(4):2990-2997.
42. Darwish A S, Grady L M, Bai P, & Weller S K (2016) ICP8 Filament Formation Is Essential for Replication Compartment Formation during Herpes Simplex Virus Infection. J Virol 90(5):2561-2570.
43. Hyman R W, Oakes J E, & Kudler L (1977) INVITRO REPAIR OF PREEXISTING NICKS AND GAPS IN HERPES-SIMPLEX VIRUS-DNA. Virology 76(1):286-294.
44. Wilkie N M (1973) SYNTHESIS AND SUBSTRUCTURE OF HERPESVIRUS DNA-DISTRIBUTION OF ALKALI-LABILE SINGLE-STRAND INTERRUPTIONS IN HSV-1 DNA. Journal of General Virology 21(December):453-467.
45. Smith S, Reuven N, Mohni K N, Schumacher A J, & Weller S K (2014) Structure of the Herpes Simplex Virus 1 Genome: Manipulation of Nicks and Gaps Can Abrogate Infectivity and Alter the Cellular DNA Damage Response. J Virol 88(17):10146-10156.
46. Wileman T (2007) Aggresomes and pericentriolar sites of virus assembly: Cellular defense or viral design? Annu Rev Microbiol, Annual Review of Microbiology, (Annual Reviews, Palo Alto), Vol 61, pp 149-167.
47. Wileman T (2006) Aggresomes and autophagy generate sites for virus replication. Science 312(5775):875-878.
48. Nozawa N, Yamauchi Y, Ohtsuka K, Kawaguchi Y, & Nishiyama Y (2004) Formation of aggresome-like structures in herpes simplex virus type 2-infected cells and a potential role in virus assembly. Exp Cell Res 299(2):486-497.
49. Gaspar M & Shenk T (2006) Human cytomegalovirus inhibits a DNA damage response by mislocalizing checkpoint proteins. Proc Natl Acad Sci USA 103(8):2821-2826.
50. Gelman I H & Silverstein S (1986) COORDINATE REGULATION OF HERPES-SIMPLEX VIRUS GENE-EXPRESSION IS MEDIATED BY THE FUNCTIONAL INTERACTION OF 2 IMMEDIATE EARLY GENE-PRODUCTS. J Mol Biol 191(3):395-409.
51. Everett R D (1984) TRANS ACTIVATION OF TRANSCRIPTION BY HERPES-VIRUS PRODUCTS—REQUIREMENT FOR 2 HSV-1 IMMEDIATE-EARLY POLYPEPTIDES FOR MAXIMUM ACTIVITY. Embo Journal 3(13):3135-3141.
52. Sacks W R & Schaffer P A (1987) DELETION MUTANTS IN THE GENE ENCODING THE HERPES-SIMPLEX VIRUS TYPE-1 IMMEDIATE-EARLY PROTEIN ICP0 EXHIBIT IMPAIRED GROWTH IN CELL-CULTURE. J Virol 61(3):829-839.
53. Everett R D (1989) CONSTRUCTION AND CHARACTERIZATION OF HERPES-SIMPLEX VIRUS TYPE-1 MUTANTS WITH DEFINED LESIONS IN IMMEDIATE EARLY GENE-1. Journal of General Virology 70:1185-1202.
54. Preston C M (2000) Repression of viral transcription during herpes simplex virus latency. Journal of General Virology 81:1-19.
55. Yao F & Schaffer P A (1994) PHYSICAL INTERACTION BETWEEN THE HERPES-SIMPLEX VIRUS TYPE-1 IMMEDIATE-EARLY REGULATORY PROTEINS ICP0 AND ICP4. J Virol 68(12):8158-8168.
56. Liu M Y, et al. (2010) ICP0 Antagonizes ICP4-Dependent Silencing of the Herpes Simplex Virus ICP0 Gene. PLoS One 5(1):16.
57. Roizman B, Knipe D M, & Knipe D M Whitley R J (20012007) Herpes Simplex Viruses and Their Replication. Fields Virology, eds Knipe D M & Howley P M (Lippencott Williams & Wilkins, Philadelphia), 4th 5th Ed Vol 2, pp 2399-24572501-2601.
Brown E J & Baltimore D (2003) Essential and dispensable roles of ATR in cell cycle arrest and genome maintenance. Genes Dev 17(5):615-628.
58. Stracker T H, Usui T, & Petrini J H (2009) Taking the time to make important decisions: the checkpoint effector kinases Chk1 and Chk2 and the DNA damage response. DNA Repair (Amst) 8(9):1047-1054.
59. Edwards T G, Helmus M J, Koeller K, Bashkin J K, & Fisher C (2013) Human papillomavirus episome stability is reduced by aphidicolin and controlled by DNA damage response pathways. J Virol 87(7):3979-3989.
60. Tran R K, Lieu P T, Aguilar S, Wagner E K, & Bloom D C (2002) Altering the expression kinetics of VP5 results in altered virulence and pathogenesis of herpes simplex virus type 1 in mice. J Virol 76(5):2199-2205.
61. O'Driscoll M, Ruiz-Perez V L, Woods C G, Jeggo P A, & Goodship J A (2003) A splicing mutation affecting expression of ataxia-telangiectasia and Rad3-related protein (ATR) results in Seckel syndrome. Nat Genet 33(4): 497-501.
62. Alwine J C (2012) The Human Cytomegalovirus Assembly Compartment: A Masterpiece of Viral Manipulation of Cellular Processes That Facilitates Assembly and Egress. PLoS Pathog 8(9):4.
63. Murayama T, Natsuumesakai S, Shimokawa K, & Furukawa T (1986) FC RECEPTOR(S) INDUCED BY HUMAN CYTOMEGALOVIRUS BIND DIFFERENTIALLY WITH HUMAN IMMUNOGLOBULIN-G SUBCLASSES. Journal of General Virology 67:1475-1478.
64. Mirzoeva O K & Petrini J H J (2003) DNA replication-dependent nuclear dynamics of the Mre11 complex. Molecular Cancer Research 1(3):207-218.
65. Hilton B A, et al. (2015) ATR Plays a Direct Antiapoptotic Role at Mitochondria, which Is Regulated by Prolyl Isomerase Pin1. Mol Cell 60(1):35-46.
66. Wang J N, Han X Z, Feng X J, Wang Z H, & Zhang Y W (2012) Coupling Cellular Localization and Function of Checkpoint Kinase 1 (Chk1) in Checkpoints and Cell Viability. Journal of Biological Chemistry 287(30): 25501-25509.
67. Ferguson B J, Mansur D S, Peters N E, Ren H, & Smith G L (2012) DNA-PK is a DNA sensor for IRF-3-dependent innate immunity. Elife 1.
68. Postigo A, Ramsden A E, Howell M, & Way M (2017) Cytoplasmic ATR Activation Promotes Vaccinia Virus Genome Replication. Cell Reports 19(5):1022-1032.

The recitation of a listing of chemical groups in any definition of a variable herein includes definitions of that variable as any single group or combination of listed groups. The recitation of an element, an embodiment herein includes that element or embodiment as any single element or embodiment or in combination with any other element, embodiments or portions thereof.

The disclosures of each and every patent, patent application and publication cited herein are hereby incorporated herein by reference in their entirety.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A method of treating or preventing a herpesvirus infection in a subject comprising administering to the subject identified as in need thereof VE-822:

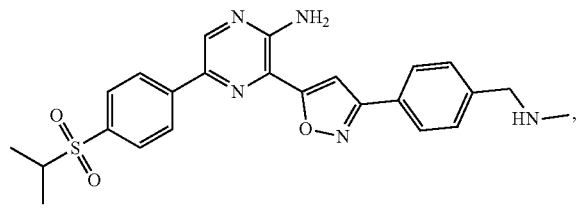 [SMILES: CNCc1ccc(-c2cc(-c3nc(-c4ccc(S(=O)(=O)C(C)C)cc4)cnc3N)on2)cc1]

or salt, hydrate or solvate thereof.

2. The method of claim 1, wherein the subject is administered PF-00477736:

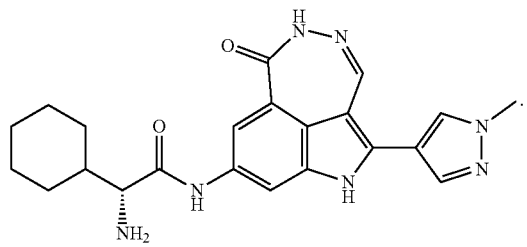 [SMILES: Cn1cc(-c2[nH]c3cc(NC(=O)[C@H](N)C4CCCCC4)cc4c3c2C=NNC4=O)cn1]

3. The method of claim 2, wherein VE-822 or salt, hydrate or solvate thereof and PF-00477736 are administered simultaneously.

4. The method of claim 2, wherein VE-822 or salt, hydrate or solvate thereof and PF-00477736 are administered sequentially.

5. The method of claim 1, wherein the herpesvirus is HSV-1 or HSV-2.

6. The method of claim 1, wherein VE-822 or salt, hydrate or solvate thereof inhibits ATR-mediated DNA-damage-checkpoint pathway.

7. The method of claim 1, wherein VE-822 or salt, hydrate or solvate thereof does not inhibit ATM.

8. The method of claim 1, wherein the herpesvirus is HSV-1, HSV-2, Varicella zoster virus, Epstein-Barr virus, human herpesvirus 6, human herpesvirus 7, Kaposi's sarcoma-associated herpesvirus, Pseudorabies virus, gaHV-2, BHV-1, or EHV-1.

9. A method for reducing HSV viral replication comprising contacting a cell with VE-822:

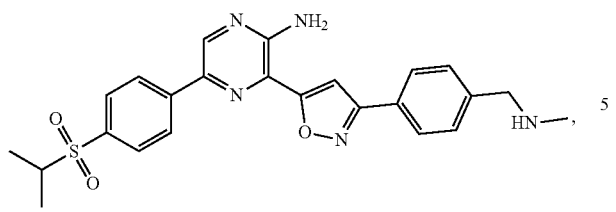
or salt, hydrate or solvate thereof.
10. A method of inhibiting HSV in a subject identified as in need of such treatment, comprising administering VE-822:
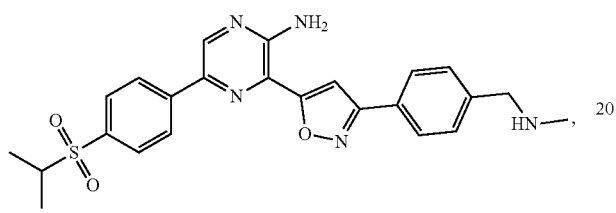
or salt, hydrate or solvate thereof.
* * * * *

UNITED STATES PATENT AND TRADEMARK OFFICE
CERTIFICATE OF CORRECTION

| | | |
|---|---|---|
| PATENT NO. | : 11,730,734 B2 | |
| APPLICATION NO. | : 16/332211 | |
| DATED | : August 22, 2023 | |
| INVENTOR(S) | : Christopher Fisher et al. | |

It is certified that error appears in the above-identified patent and that said Letters Patent is hereby corrected as shown below:

In the Claims

At Column 42, Claim 2, Lines 30-31:
"wherein the subject is administered"
Should read:
--wherein the method further comprises a step of administering--

Signed and Sealed this
Twelfth Day of December, 2023

Katherine Kelly Vidal
*Director of the United States Patent and Trademark Office*